United States Patent
Birla

(10) Patent No.: US 9,808,336 B2
(45) Date of Patent: Nov. 7, 2017

(54) TWO STAGE CELLULARIZATION STRATEGY FOR THE FABRICATION OF BIOARTIFICIAL HEARTS

(71) Applicant: Ravi K. Birla, Sugar Land, TX (US)

(72) Inventor: Ravi K. Birla, Sugar Land, TX (US)

(73) Assignee: UNIVERSITY OF HOUSTON SYSTEM, Houston, TX (US)

( * ) Notice: Subject to any disclaimer, the term of this patent is extended or adjusted under 35 U.S.C. 154(b) by 224 days.

(21) Appl. No.: 14/701,930

(22) Filed: May 1, 2015

(65) Prior Publication Data
US 2015/0335417 A1     Nov. 26, 2015

Related U.S. Application Data

(60) Provisional application No. 61/987,962, filed on May 2, 2014.

(51) Int. Cl.
*A61F 2/02*     (2006.01)
*A61F 2/08*     (2006.01)
(Continued)

(52) U.S. Cl.
CPC .............. *A61F 2/08* (2013.01); *A61L 27/225* (2013.01); *A61L 27/34* (2013.01);
(Continued)

(58) Field of Classification Search
CPC ........... A61F 2/08; A61M 1/12; A61M 1/122; C12N 5/077; C12N 5/0657; A61L 27/34; A61L 27/325; A61L 27/3604
See application file for complete search history.

(56) References Cited

U.S. PATENT DOCUMENTS

| 8,470,520 B2 | 6/2013 | Ott et al. |
| 2007/0092492 A1 | 4/2007 | Matsuda et al. |

(Continued)

FOREIGN PATENT DOCUMENTS

WO    WO-2014044321 A1    3/2014

OTHER PUBLICATIONS

Organ Procurement and Transplantation Network and Scientific Registry of Transplant Recipients. 2010 Data Report. Am J Transplant 12 Suppl 1:1-156, 2012.
(Continued)

*Primary Examiner* — Victor Nguyen
(74) *Attorney, Agent, or Firm* — Winstead PC

(57) ABSTRACT

In some embodiments, the present disclosure pertains to a method of fabricating an artificial heart muscle (AHM) patch. In some embodiments, the method includes obtaining and/or isolating cells from a subject. In some embodiments, the cells are primary cardiac cells. In some embodiments, the method further includes forming a scaffold. In some embodiments, the method includes seeding the cells in the fibrin gel scaffold. In some embodiments, the method includes culturing the cells seeded in the fibrin gel scaffold under conditions appropriate for the formation of an artificial heart muscle (AHM) patch. In some embodiments, the present disclosure pertains to a method of fabricating a bioartificial heart (BAH). In some embodiments, the present disclosure pertains to a method of treatment of cardiac tissue injury in a subject in need thereof. In some embodiments, the method includes implanting the aforementioned artificial heart muscle patch in the injured area of the subject. In some embodiments, the present disclosure relates to a method of treating end stage cardiac disease in a subject in need thereof.

5 Claims, 15 Drawing Sheets

(51) Int. Cl.
A61M 1/12 (2006.01)
C12N 5/077 (2010.01)
A61L 27/22 (2006.01)
A61L 27/34 (2006.01)
A61L 27/36 (2006.01)
A61L 27/38 (2006.01)

(52) U.S. Cl.
CPC ....... *A61L 27/3604* (2013.01); *A61L 27/3826* (2013.01); *A61L 27/3834* (2013.01); *A61M 1/12* (2013.01); *A61M 1/122* (2014.02); *C12N 5/0657* (2013.01); *A61L 2430/20* (2013.01); *A61L 2430/40* (2013.01); *C12N 2533/56* (2013.01); *C12N 2533/90* (2013.01)

(56) References Cited

U.S. PATENT DOCUMENTS

| | | | |
|---|---|---|---|
| 2008/0009830 A1 | 1/2008 | Fujimoto et al. | |
| 2009/0138074 A1 | 5/2009 | Freyman et al. | |
| 2010/0184183 A1* | 7/2010 | Schussler | A61L 27/24 435/177 |
| 2014/0328806 A1 | 11/2014 | Birla | |

OTHER PUBLICATIONS

Lloyd-Jones D et al. Heart Disease and Stroke Statistics—2010 Update: A Report From the American Heart Association. Circulation 121:e46-e215, 2010.
Hunt SA, et al. ACC/AHA 2005 guideline update for the diagnosis and management of chronic heart failure in the adult: A report of the American college of cardiology/american heart association task force on practice guidelines (writing committee to update the 2001guidelines for the evaluation and management of heart failure). J Am Col Cardiol 46:e1-82, 2005.
Rosamond W, et al. Heart disease and stroke statistics—2008 update: A report from the American Heart Association Statistics Committee and Stroke Statistics Subcommittee. Circulation 117:e25-146, 2008.
Olson EN. A decade of discoveries in cardiac biology. Nat Med 10:467-474, 2004.
Sipe JD. Tissue engineering and reparative medicine. Ann N Y Acad Sci 961:1-9, 2002.
Khait L, et al. Getting to the heart of tissue engineering. J CardiovascTransl Res 1:71-84, 2008.
Rustad KC, et al. Strategies for organ level tissue engineering. Organogenesis 6:151-157, 2010.
Atala A. Tissue engineering and regenerative medicine: Concepts for clinical application. Rejuvenation Res 7:15-31, 2004.
Nerem RM. Tissue engineering: The hope, the hype, and the future. Tissue engineering 12:1143-1150, 2006.
Fisher MB, Mauck RL. Tissue engineering and regenerative medicine: Recent innovations and the transition to translation. Tissue Eng Part B Reviews 19:1-13, 2013.
Chiu LL, et al. Cardiac tissue engineering: Current state and perspectives. Front Biosci (Landmark Ed) 17:1533-1550, 2012.
Curtis MW, Russell B. Cardiac tissue engineering. J Cardiovasc Nurs 24:87-92, 2009.
Hecker L, Birla RK. Engineering the heart piece by piece: State of the art in cardiac tissue engineering. Regen Med 2:125-144, 2007.
Evers R, et al. Fabrication of functional cardiac, skeletal, and smooth muscle pumps in vitro. Artif Organs 35:69-74, 2011.
Birla RK, et al. Methodology for the formation of functional, cellbased cardiac pressure generation constructs in vitro. In Vitro Cell Dev Biol Anim 44:340-350, 2008.
Lu TY, et al. Repopulation of decellularized mouse heart with human induced pluripotent stem cell-derived cardiovascular progenitor cells. Nat Commun 4:2307, 2013.
Ott HC, et al. Perfusion-decellularized matrix: Using nature's platform to engineer a bioartificial heart. Nat Med 14:213-221, 2008.
Ott HC, et al. Regeneration and orthotopic transplantation of a bioartificial lung. Nat Med 16:927-933, 2010.
Song JJ, et al. Regeneration and experimental orthotopic transplantation of a bioengineered kidney. *Nat Med* 19:646-651, 2013.
Elliott MJ, et al. Stem-cell-based, tissue engineered tracheal replacement in a child: A 2-year follow-up study. Lancet 380:994-1000, 2012.
Macchiarini P, et al. Clinical transplantation of a tissue-engineered airway. Lancet 372:2023-2030, 2008.
Atala A, et al. Tissue-engineered autologous bladders for patients needing cystoplasty. Lancet 367:1241-1246, 2006.
Tao ZW, et al. Attenuation of myocardial injury due to oxygen free radicals (ofr) by pretreatment with ofr or calcitonin gene-related peptide. Zhongguo yao li xue bao(Acta pharmacol Sin) 18:312-316, 1997.
Evans HJ, et al. Novel 3d culture system for study of cardiac myocyte development. Am J Physiol Heart Circ Physiol 285:H570-578, 2003.
Yildirim Y, et al. Development of a biological ventricular assist device: Preliminary data from a small animal model. *Circulation* 116:116-23, 2007.
Yost MJ, et al. A novel tubular scaffold for cardiovascular tissue engineering. Tissue Eng 10:273-284, 2004.
Lee EJ, et al. Engineered cardiac organoid chambers: Toward a functional biological model ventricle. Tissue Eng Part A 14:215-225, 2008.
Maher B. Tissue engineering: How to build a heart. *Nature* 499:20-22, 2013.
Guo XM, et al. Creation of engineered cardiac tissue in vitro from mouse embryonic stem cells. *Circulation* 113:2229-2237, 2006.
Zimmermann WH, et al. Engineered heart tissue grafts improve systolic and diastolic function in infarcted rat hearts. Nat Med 12:452-458, 2006.
Sekine H, et al. Cardiac cell sheet transplantation improves damaged heart function via superior cell survival in comparison with dissociated cell injection. Tissue Eng Part A 17:2973-2980, 2011.
Copeland JG, et al. Cardiac Replacement with a Total Artificial Heart as a Bridge to Transplantation. N. Engl. J. Med. 2004;351:859-67.
Bond AE, et al. CE Credit: The Left Ventricular Assist Device. Am. J.Nurs. 2003;103:32-41.
Platis A, Larson DF. CardioWest temporary total artificial heart. Perfusion [Internet]. Circulatory Sciences Graduate Perfusion Program, College of Medicine, University of Arizona, Tucson, AZ, USA; 2009;24:341-6.
Archundia A, et al. Direct cardiac injection of G-CSF mobilized bone-marrow stem-cells improves ventricular function in old myocardial infarction. Life Sci. [Internet]. 2005;78:279-83.
Hayashi C, et al. Osteoblastic bone formation is induced by using nanogel-crosslinking hydrogel as novel scaffold for bone growth factor. J. Cell. Physiol. [Internet]. Wiley Subscription Services, Inc., A Wiley Company; 2009;220:1-7.
Langer R, Vacanti JP. Tissue Engineering. Science (80-. ). [Internet], American Association for the Advancement of Science; 1993;260:920-6.
Shachar M, et al. Effects of mechanical stimulation induced by compression and medium perfusion on cardiac tissue engineering. Biotechnol. Prog. [Internet], Wiley Subscription Services, Inc., A Wiley Company; 2012 [cited May 10, 2013];28:1551-9.
Evers R, et al. Fabrication of Functional Cardiac, Skeletal, and Smooth Muscle Pumps in Vitro. [Internet], Artif. Organs. Wiley-Blackwell; 2011. p. 69-74.
Birla RK, et al. Tissue-engineered heart valve prostheses: "state of the heart." Regenerative Medicine 2008;3:399+.
Khait L, Birla R. Cell-based cardiac pumps and tissue-engineered ventricles. Regen. Med. [Internet]. 2.4 2007 [cited Apr. 18, 2013].
Blan NR, Birla RK. Design and fabrication of heart muscle using scaffold-based tissue engineering. J. Biomed. Mater. Res. Part A [Internet], Wiley Subscription Services, Inc., A Wiley Company; 2008;86A: 195-208.

(56) References Cited

OTHER PUBLICATIONS

Huang Y-C, et al Contractile three-dimensional bioengineered heart muscle for myocardial regeneration. J. Biomed. Mater. Res. Part A [Internet]. Wiley Subscription Services, Inc., A Wiley Company; 2007;80A:719-31.

Gilbert TW, et al. Decellularization of tissues and organs. Biomaterials [Internet]. 2006;27:3675-83.

Black LD, et al. Perfusion-decellularized matrix: using nature's platform to engineer a bioartificial heart. Nat. Med. [Internet], 2008; 14:213+.

Rakusan K, et al. Cell size and capillary supply of the hypertensive rat heart: quantitative study. Basic Res. Cardiol. [Internet], Steinkopff-Verlag; 1984;79:389-95.

Chen H-C, Hu Y-C. Bioreactors for tissue engineering. Biotechnol. Lett. [Internet]. Springer Netherlands; 2006;28:1415-23.

Shimaoka M, et al Conformational Regulation of Integrin Structure and Function. Annu. Rev. Biophys. Biomol. Struct. [Internet]. Annual Reviews; 2002;31:485-516.

McGinn OJ, et al. Modulation of integrin ?4?1 by ADAM28 promotes lymphocyte adhesion and transendothelial migration. Cell Biol. Int. [Internet], 2011;35:1043-53.

Amado LC, et al. Cardiac repair with intramyocardial injection of allogeneic mesenchymal stem cells after myocardial infarction. Proc. Natl. Acad. Sci. U. S. A. [Internet]. 2005;102:11474-9.

Baar K, et al. Self-organization of rat cardiac cells into contractile 3-D cardiac tissue. FASEB J. [Internet]. 2004; 10.1096/fj.04-2034fje.

Banerjee I, et al. Determination of cell types and numbers during cardiac development in the neonatal and adult rat and mouse. 2007; Am J Physiol Heart Circ Physiol 293:H1883-H1891.

Grinnell F. Manganese-dependent cell-substratum adhesion. J. Cell Sci. [Internet]. 1984;65:61-72.

Ketchedjian A, et al. Recellularization of Decellularized Allograft Scaffolds in Ovine Great Vessel Reconstructions. Ann. Thorac. Surg. [Internet]. 2005 [cited Apr. 22, 2013];79:888-96.

Members WG, et al. Heart Disease and Stroke Statistics—2012 Update. Circulation [Internet]. 2012;125:e2-e220.

* cited by examiner

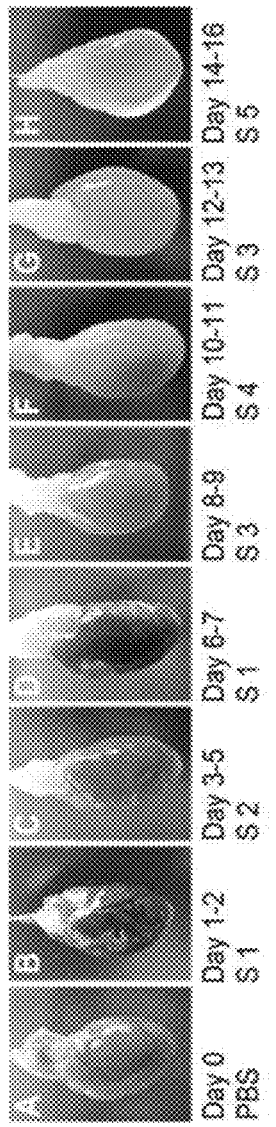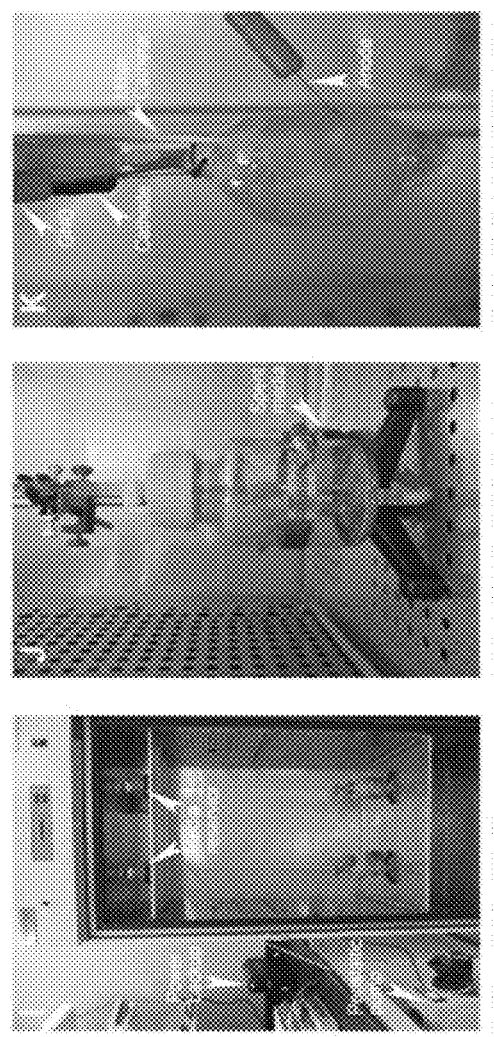
Fig. 2A Fig. 2B Fig. 2C Fig. 2D Fig. 2E Fig. 2F Fig. 2G Fig. 2H
Day 0 / Day 1-2 / Day 3-5 / Day 6-7 / Day 8-9 / Day 10-11 / Day 12-13 / Day 14-16
PBS / S1 / S2 / S1 / S3 / S4 / S3 / S5
Fig. 2I Inside the incubator
Fig. 2J Inside the culture vessel
Fig. 2K Detect ECG and LV pressure

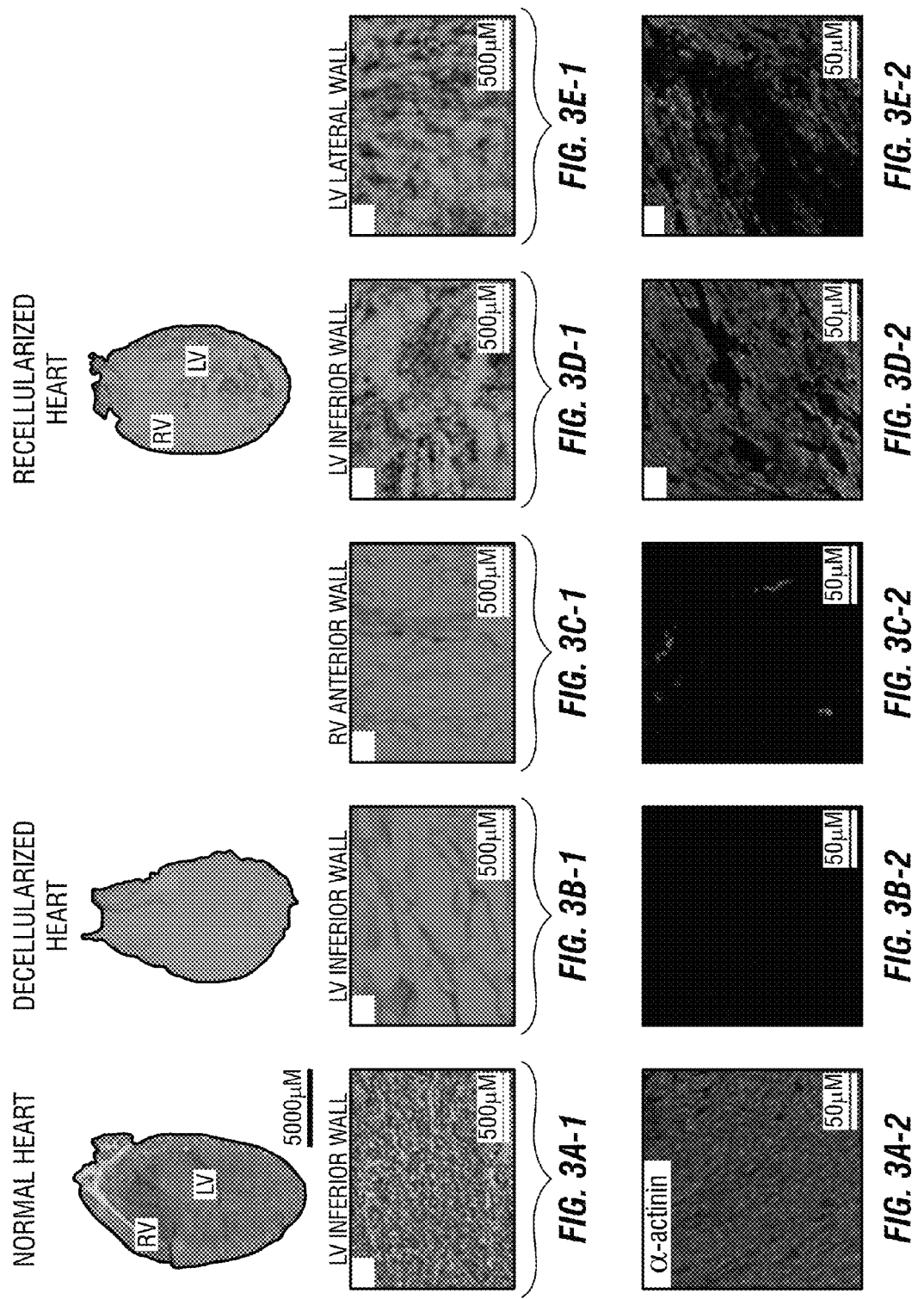

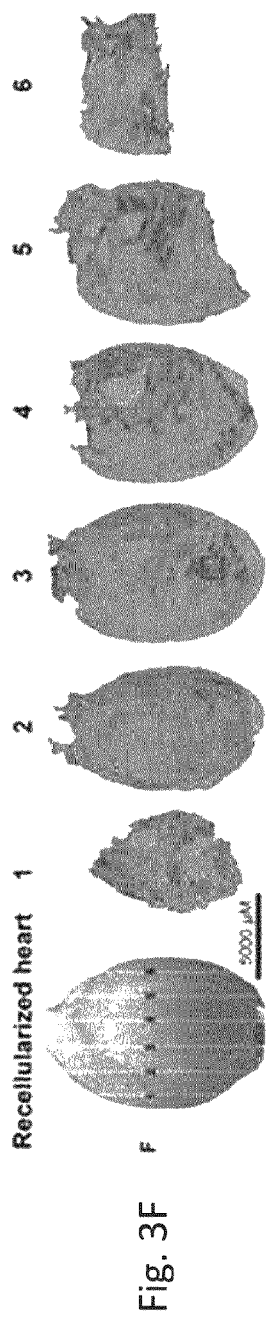
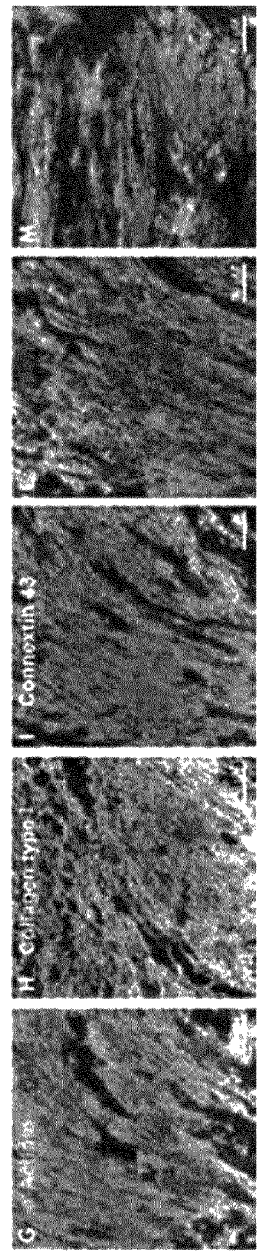
Fig. 3F  Fig. 3G  Fig. 3H  Fig. 3I  Fig. 3J  Fig. 3K

TWO STAGE CELLULARIZATION STRATEGY FOR THE FABRICATION OF BIOARTIFICIAL HEARTS

CROSS REFERENCE TO RELATED APPLICATION

This application claims priority to U.S. Provisional Application No. 61/987,962 filed on May 2, 2014. The entirety of the aforementioned application is incorporated herein by reference.

STATEMENT REGARDING FEDERALLY-SPONSORED RESEARCH

This invention was made, at least in part, with U.S. government support under grant No. R01-EB011516 awarded by the National Institute of Health. The U.S. government may have certain rights in this invention.

BACKGROUND

Cardiovascular disease adversely affects lives of millions of patients around the globe. The economic impact is often in the order of hundreds of billions of dollars. For example, in the United States alone, approximately 5.7 million people live with heart disease and management of these patients accrues a cost of nearly 34 billion per year. Over 50% of patients with heart disease do not respond to current pharmacological therapies. To date heart transplantation is the most effective option for patients suffering from end stage heart failure. However, in addition to the logistical and medical complexity of this therapeutic option, donor organ shortage represents a major limitation, and up to 20% of the patients die while on the waiting list. Thus, there exists a need to circumvent these current clinical limitations by engineering an artificial heart that displays functional and morphological properties of the native heart and remains viable after implantation.

SUMMARY

In some embodiments, the present disclosure pertains to a method of fabricating an artificial heart muscle (AHM) patch. In some embodiments, the method comprises obtaining and/or isolating cells from a subject. In some embodiments, the cells are primary cardiac cells. In some embodiments, the subject is a mammal. In some embodiments, the cells obtained and/or isolated are neonatal cardiomyocytes. In some embodiments, the neonatal cardiac myocytes are mammalian neonatal cardiac myocytes. In some embodiments, the method further comprises forming a scaffold. In some embodiments, the scaffold is formed from fibrin gel. In some embodiments, the scaffold is formed by layering the fibrin on a surface coated with a silicone elastomer. In some embodiments, the fibrin gel is mixed with saline and culture media containing thrombin. In some embodiments, the method further comprises adding a protease inhibitor. In some embodiments, the protease inhibitor is episilon-aminocaproic acid. In some embodiments, the method further comprises placing means for anchoring the patch on the surface coated with the silicone elastomer. Various means of anchoring may be used compatibly with the methods disclosed herein. In an embodiment, the means for anchoring used are minutien pins. In some embodiments, the anchoring guides the morphology of the fabricated patch.

In some embodiments, the method comprises culturing the cells seeded in the fibrin gel scaffold under conditions appropriate for the formation of an artificial heart muscle (AHM) patch. In some embodiments, the method further comprises assessing the structure and function of the artificial heart muscle patch.

In some embodiments, the present disclosure pertains to a method of fabricating a bioartificial heart (BAH). In some embodiments, the method comprises obtaining and/or isolating cells from a subject. In some embodiments, the cells are primary cardiac cells. In some embodiments, the subject is a mammal. In some embodiments, the cells obtained and/or isolated are neonatal cardiomyocytes. In some embodiments, the neonatal cardiac myocytes are mammalian neonatal cardiac myocytes. In some embodiments, the method further comprises obtaining a scaffold. In some embodiments, the scaffold is obtained by decellularization of a heart tissue. In some embodiments, the method further comprises transplanting the cells within the scaffold. In some embodiments, the transplanting the cells is by direct cell transplant. In some embodiments, the direct cell transplant comprises delivering the cells to the acellular scaffold by a plurality of direct injections. In some embodiments, the method further comprises culturing the scaffold transplanted with the cells in a perfusion culture apparatus. In some embodiments, the perfusion culture apparatus mimics in vivo conditions.

In some embodiments, the present disclosure pertains to a method of fabricating bioartificial heart (BAH). In some embodiments, the method comprises fabricating at least one artificial heart muscle (AHM) patch by the aforementioned disclosed method. In some embodiments, the method further comprises obtaining and/or preparing a scaffold. In some embodiments, the scaffold is obtained and/or prepared by decellularization of a heart. In some embodiments, the heart is a mammalian heart. In some embodiments, the method further comprises suturing the at least one AHM patch around the decellularized scaffold to form a construct. In some embodiments, the at least one AHM partially covers the scaffold. In some embodiments, the at least one AHM completely covers the scaffold. In some embodiments, the method further comprises culturing the construct under conditions appropriate for the formation of the BAH.

In some embodiments, the present disclosure pertains to a method of treatment of cardiac tissue injury in a subject in need thereof. In some embodiments, the method includes implanting the aforementioned AHM in the injured area of the subject.

In some embodiments, the present disclosure relates to a method of treating end stage cardiac disease in a subject in need thereof. In some embodiments, such a method comprises transplanting a bioartificial heart fabricated by any of the methods disclosed herein in the subject. In some embodiments, the transplanted bioartificial heart replaces the function of the natural heart.

Additional embodiments of the present disclosure pertain to a medicament comprising the aforementioned composition. In some embodiments the medicament further comprises at least one agent from the group consisting of survival factors, growth factors, pharmacological agents, angiogenic factors, beta-blockers or ACE inhibitors.

The above objects and other objects, features, and advantages of the present invention are readily apparent from the following detailed description of the best mode for carrying out the invention when taken in conjunction with the accompanying drawings.

BRIEF DESCRIPTION OF THE FIGURES

FIGS. 2A-2K show heart scaffold preparations, BAH fabrication and functional assessment. Adult rat hearts were submerged in different detergent solutions over a two week period, leading to complete removal of cellular components, leaving behind an intact scaffold (FIG. 2A-FIG. 2G). Culture media was maintained in a reservoir and positioned 100 cm above the heart chamber, which was used to house BAHs (FIG. 2I). Gravity flow was used for media perfusion and spent media was recycled to the reservoir and replaced every two days (FIG. 2J). ECG and ventricular pressure were measured within the incubator (FIG. 2K).

FIGS. 3A-1-3K show a comparison of Normal, Decellularized, and Recellularized hearts using histology and immunofluorescence. Whole heart sections stained by Masson's trichrome or immunofluorescence from normal, decellularized and recellularied hearts were compared. From the left ventricular (LV) inferior wall of a normal heart (FIG. 3A1 and FIG. 3A2); from the LV inferior wall of a decellularized heart (FIG. 3B1 and FIG. 3B2); from the (right ventricular) RV wall of recellularized heart (FIG. 3C1 and FIG. 3C2); from the LV inferior wall of a recellularized heart (FIG. 3D1 and FIG. 3D2); and, from the LV lateral wall of a recellularized heart (FIG. 3E1 and FIG. 3E2). Sequential sections stained by Masson trichrome from RV to LV of a recellularied heart (FIG. 3F). Immunofluorescent images illustrating α-actinin, collagen type I, connexin 43, N-cadherin and vWF from the inferior wall of a recellularized heart (FIG. 3G-FIG. 3K).

FIG. 11A shows the decellularized scaffold and FIG. 11B shows the cell rich layer and fibrin scaffold.

DETAILED DESCRIPTION

Figure 1:
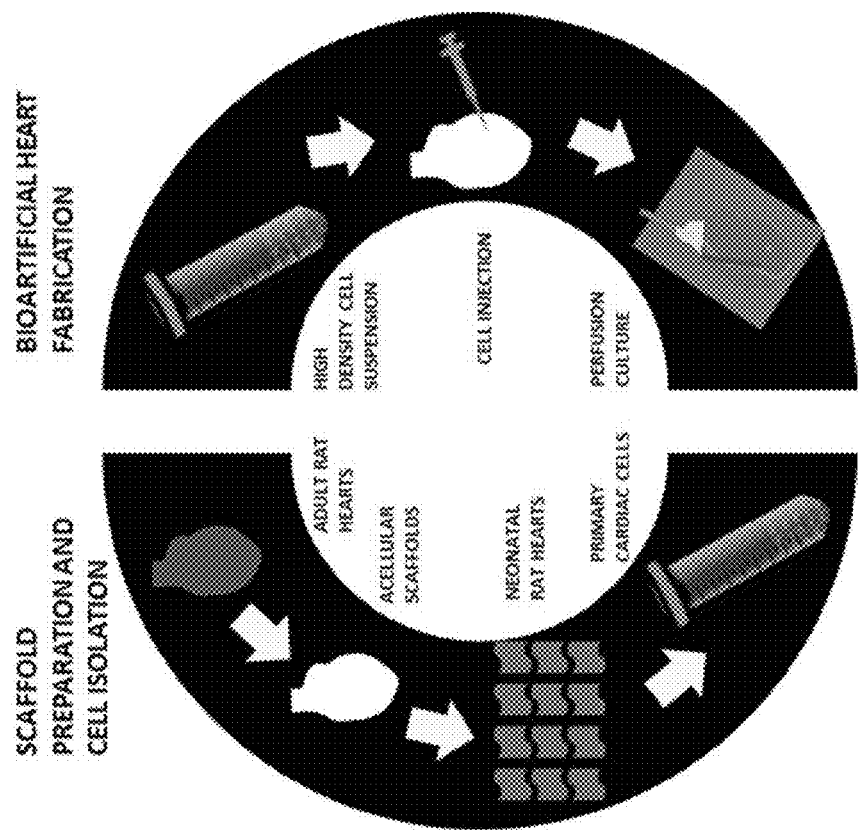
FIG. 1 shows a schematic depicting Bioartificial Heart (BAH) Fabrication. Rodent hearts were decellularized and used as scaffolds to support BAH fabrication. Primary cardiac myocytes were isolated from 2-3 day old rat hearts and used for scaffold cellularization. In order to promote BAH fabrication primary cardiac myocytes were suspended in a small volume of cell culture medium at transplanted by direct injection to the acellular scaffold using a syringe. The cellularized scaffolds were cultured in a perfusion chamber and used for functional assessment at defined time points.

It is to be understood that both the foregoing general description and the following detailed description are exemplary and explanatory only, and are not restrictive of the invention, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that comprise more than one unit unless specifically stated otherwise. Parameters disclosed herein (e.g., temperature, time, concentration, etc.) may be approximate.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials defines a term in a manner that contradicts the definition of that term in this application, this application controls.

"Angiogenesis" as used herein, generally refers to the growth of blood vessels in the three-dimensional artificial cardiac patch construct. The angiogenesis may occur in response to a stimulus, for instance, in response to administration of an effective amount of an angiogenic factor.

The term "angiogenic factor" as used herein shall be given its ordinary meaning and shall refer to a molecule capable of activating or otherwise promoting angiogenesis.

The term "cardiac patch" as used herein shall be given its ordinary meaning and shall refer to tissue of the heart, for example, the epicardium, myocardium or endocardium, or portion thereof, of the heart.

The term "cardiac tissue injury" as used herein shall be given its ordinary meaning and shall refer to a cardiac tissue that is, for example, ischemic, infarcted, reperfused, or otherwise focally or diffusely injured or diseased. Injuries associated with a cardiac tissue include any areas of abnormal tissue in the heart, including any areas of abnormal tissue caused by a disease, disorder or injury and includes damage to the epicardium, endocardium and/or myocardium. Non-limiting examples of causes of cardiac tissue injuries include acute or chronic stress (e.g., systemic hypertension, pulmonary hypertension or valve dysfunction), atheromatous disorders of blood vessels (e.g., coronary artery disease), ischemia, infarction, inflammatory disease and cardiomyopathies, myocarditis or congestive heart failure.

The term "Subject", "Animal", or "Mammal," as used herein, includes animals and humans. Thus, when referring to processes such as harvesting tissue from an animal, it is intended that the animal can be a human. Although at times reference may be made herein to "an animal or human," this is not intended to imply that the term "animal" does not include a human.

Additionally, the term as Subject" or "Recipient," as used herein, includes individuals who require intervention or manipulation due to a disease state, treatment regimen or experimental design.

"Biocompatible," as used herein, generally refers to an autologous cell or tissue that originates or is derived from the subject or recipient.

The phrases "conditions suitable for cells to self-organize" or "appropriate cell culture conditions" for a suitable cell type, as used herein, generally refers to an environment with conditions of temperature, pressure, humidity, nutrient and waste exchange, and gas exchange that are permissive for the survival and reproduction of the cells. With respect to any particular type of cell, an environment suitable for growth may require the presence of particular nutrients or growth factors needed or conducive to the survival and/or reproduction of the cells.

"Engineered cardiac tissue construct" or "cardiac patch", or "artificial cardiac patch construct" as used herein, generally refers to three dimensional mass of living mammalian tissue produced primarily by growth in vitro on a substrate. The construct may include one or more types of cells or tissues. For example, the construct may be made up of myocytes cultured in conjunction with other cell types, such as endocardial cells, vascular smooth muscle cells, vascular endothelium, fibroblast, and adrenergic cells, or various subsets of those cell types. The term also encompasses a three-dimensional mass of living mammalian tissue produced at least in part by growth in vivo on a substrate. More particularly, constructs may include two or three-dimensional tissue which share critical structural and functional characteristics with intact cardiac tissue, such as distinctive multicellular organization and oriented contractile function.

"Real Cardiac Layer," as used herein, generally refers to a self-organized monolayer of the neonatal cardiac cells and naturally produced extracellular matrix on top of the biological support scaffold.

As used herein, the terms "treat," "treatment" and "treating" shall be given their ordinary meaning and shall refer to the reduction or amelioration of the progression, severity, and/or duration of a cardiac tissue injury or a symptom thereof. Treatment as used herein includes, but are not limited to, preserving the injured cardiac tissue, regenerating new cardiac tissue, increasing blood flow to the injured tissue, increasing myocardial perfusion, improving global cardiac function (e.g., stroke volume, ejection fraction, and cardiac output) and regional cardiac function (e.g., ventricular wall thickening, segmental shortening and heart pumping).

Cardiovascular disorders are prevalent in today's society and adversely affect the lives of millions of patients around the globe. The economic impact is often in the order of hundreds of billions of dollars. This epidemic is progressively worsening with an aging population and an increase in obesity. A variety of heart treatment modalities have been explored and are clinically available. These include mechanical assist devices used to bypass or replace a failing heart. Left ventricular assist devices (LVAD) are mechanical pumps designed to increase cardiac output. Similarly, total artificial hearts (TAH) are mechanical pumps designed to bypass the function of the entire heart, effectively serving as a bridge to heart transplant. However, both LVAD and TAH are limited by biocompatibility, device failure, and absence of bio-integration. Pharmaceutical interventions developed to combat heart disease include ACE inhibitors, blood thinners, calcium channel blockers, vasodilators, diuretics, etc. Unfortunately, the pharmaceutical agents typically treat the symptoms of heart disease and do little to combat the underlying issue of damaged cardiac tissue. Moreover 50% of patients with heart disease do not respond to current pharmacological therapies.

Presently, the long term solution to heart failure is organ transplantation. However, this option suffers from both logistical and medical complexities. Donor organ shortage represents a major limitation to this approach, with up to 20% patients dying on the waiting list. Furthermore, due to the rapid deterioration of excised tissue, donor hearts must be used within several hours of explanation. This limitation adds to reducing efficacy of treatment of end stage heart failure. Moreover, donor and recipient must be matched for blood type and body size in order to reduce the risk of rejection. The lack of donor hearts, along with the difficulty of scheduling and prohibitive costs of heart transplants contributes to inadequacy of heart transplant procedures as effective means of cardiovascular disease treatment. Thus, there exists a need in the art to develop a treatment modality that would circumvent the aforementioned problems in treating cardiac disease.

In particular, exploiting tissue engineering strategies would enable fabrication of artificial tissue would be useful in fulfilling this need existing in the art. Tissue engineering is an interdisciplinary field applying principles of engineering to biological components. In the field of tissue engineering, a combination of cells, scaffolds and/or bioreactors are used to create a construct designed to emulate native tissues. Complex biomimetic tissues can be created in vitro using combinations of cells, scaffolds, and bioreactors, which mimic in vivo conditions. Thus tissue engineering provides many promising potential research avenues for treatment alternatives to conventional and existing therapies.

In some embodiments, the present disclosure pertains to a method for fabricating a 3D-AHM comprising culturing neonatal cardiac myocytes within a suitable 3D scaffold, resulting in an artificial tissue that replicates a partial subset or a complete set of mammalian heart muscle functions. In some embodiments, the method comprises evaluation of physiological stimulation (mechanical stretch, electrical stimulation, and perfusion) to guide 3D tissue formation and function. In some embodiments, the 3D-AHMs may be used clinically to patch areas of myocardial infarction or other cardiac disorders. In addition, these 3D-AHM models provide a platform for detailed study of critical events in organogenesis, such as establishment of cell-cell communication, cytoarchitecture and extracellular matrix formations.

In some embodiments, the present disclosure defines conditions to support the fabrication of a BAH. The field of tissue engineering has progressed to a point where researchers are now able to endeavor into the possibility of whole organ engineering. The fabrication of complex organs like BAHs is associated with numerous scientific and technological challenges. In some embodiments, the present disclosure provides a framework for BAH fabrication and describes critical methodology necessary for whole organ engineering.

In some embodiments, the present disclosure pertains to an appropriate scaffold and a method of creating the scaffold for the fabrication of BAH. The scaffold may comprise numerous biomaterials. In some embodiments, the scaffold comprises a decellularized heart. In some embodiments, the scaffold comprises fibrin, chitosan, collagen, alginate, acellular grafts, matrigel.

While considerable progress has been made in biomaterial development, the technology has not progressed to the point where scaffolds for complex organs like hearts can be fabricated. Alternative strategies for the manufacture of a scaffold that can be used to support tissue and organ fabrication need to be employed. In some embodiments of the present disclosure pertains to a decellularization strategy for the fabrication of a scaffold. The premise of this strategy is to make use of mammalian tissue and completely remove all cellular material; this process is referred to as decellularization. After decellularization, the intact extracellular matrix left behind, can be used to support tissue and organ fabrication. The decellularization process is illustrated in FIGS. 2A-2H. Over a course of several days; freshly isolated hearts were exposed to a series of detergents that gradually lysed cardiac cells (FIGS. 3B1 and 3B2). This technique was efficient in producing scaffolds to support BAH fabrication.

In an embodiment, the present disclosure pertains to recellularization of the acellular or decellularlized scaffold for the fabrication of the BAH. In some embodiments, the recellularization comprises injecting primary cardiac cells within the acellular scaffold. In some embodiments, the recellularization comprises placing an artificial heart (AHM) patch around the acellular scaffold. In some embodiments, the artificial heart muscle (AHM) patch is sutured around the acellular scaffold. In some embodiments, the artificial heart muscle (AHM) patch comprises primary cardiac cells and fibrin gel. In some embodiments, primary cardiac cells are neonatal cardiac myocytes. Neonatal cardiac myocytes represent critical tools during early stage development. There is a vast body of literature demonstrating the feasibility of primary cardiac myocytes in cardiac tissue engineering. Therefore, primary cardiac cells provide an excellent platform to understand the variables that affect BAH fabrication, formation and function.

In terms of distribution and positioning of these cells in 3D culture, the recellularization strategy for the scaffold represents a significant scientific challenge in organ engineering. This problem is significant for any tissue engineering application and is exponentially greater for organ fabrication applications. Development of new, novel and more efficient cellularization strategies remains an area of opportunity for organ fabrication, particularly in the case of hearts. In addition, new methods need to be developed to increase cellular adhesion to the underlying matrix, which in turn will lead to an increase in cellular retention.

In some embodiments of the present disclosure the recellularization of the decellularized scaffold comprises direct cell transplantation. In an embodiment, the direct cell transplantation comprises delivering the isolated cells to the decellularlized or acellular scaffold using multiple injections of a syringe. While this strategy is not exact and a significant number of cells are still lost due to the cell suspension going into the ventricular chambers or spilling out, direct cell transplantation strategies have proven efficient in establishing organ level functionality. In some embodiments of the present disclosure, the direct cell transplantation strategy results in a level of organ function, as demonstrated by ECG and pressure measurements, thereby demonstrating that direct cell transplantation may be an efficient strategy for BAH fabrication.

In some embodiments the present disclosure pertains to the maintenance of fabricated BAH in vitro. During normal mammalian function, the heart is exposed to a myriad of complex signals, including electromechanical cues, fluid stresses, and changes in the hormonal and growth factor environment. There are temporal and spatial variations in all of these signals, which in turn regulate the phenotype of mammalian hearts during normal physiological culture. It is fairly obvious that during BAH culture, there is a need to recapitulate this complex in vivo culture environment during in vitro culture. In some embodiments, the present disclosure pertains to providing a perfusion culture apparatus to support BAH culture in vitro. The existing prior art systems only provides continuous media perfusion and lacks many other physiological signals. The present disclosure relates to a perfusion system that has proven efficient to support BAH culture and is designed to increase the degree of complexity of the system to accommodate delivery of additional signals.

Figure 4A:
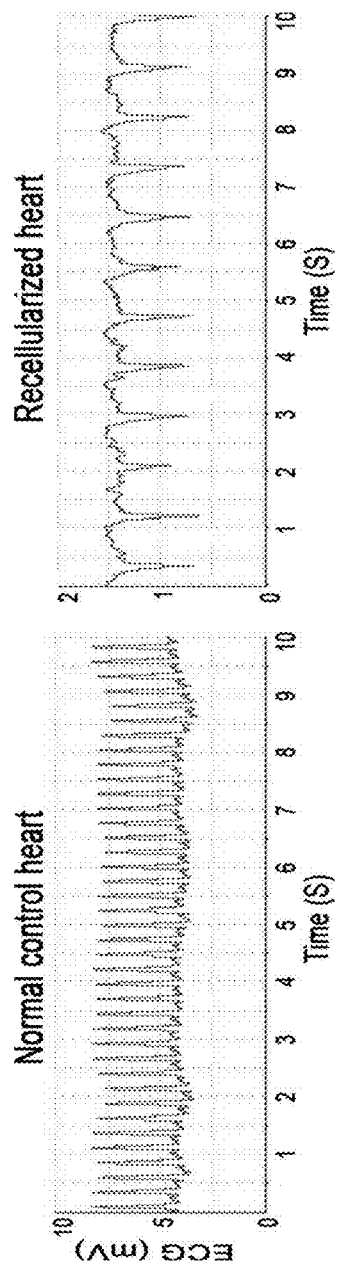
FIGS. 4A-4B shows electrocardiogram (ECG) (FIG. 4A) and Ventricular Pressure (FIG. 4B) comparison for normal versus the fabricated BAH. ECG and Left and Right ventricular pressures were measured from a normal control heart and from a recellularized heart.
Figure 4B:
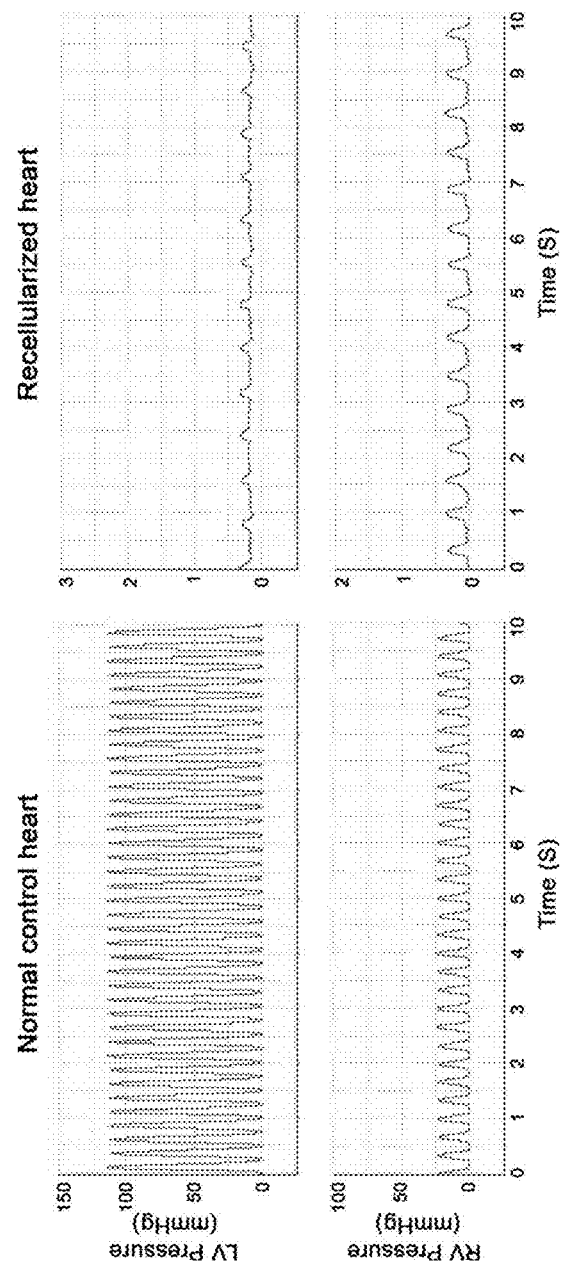

In some embodiments, the present disclosure pertains to testing the functionality of the BAH fabricated by the methods disclosed herein. In some embodiments of the present disclosure, the functionality of the BAH was assessed in terms of functional metrics such as ECG and left and right ventricle pressures (FIGS. 4A-4B). In addition, several histological markers like, α-actinin, collagen type I, connexin 43, N-cadherin and vWF were assessed (FIG. 13). In some embodiments, the fabricated BAH exhibited a partial subset of functional properties of normal mammalian hearts.

In summary, the present disclosure, in some embodiments, pertains to a method to support the fabrication of a BAH that replicates a partial subset or complete set of mammalian heart functions. In some embodiments, the present disclosure relates to a framework and defines the key technologies that are necessary for BAH fabrication. Furthermore, the present disclosure also identifies critical scientific and technological challenges that need to be overcome in order to move the field of organ engineering forward, as applied to BAHs.

In some embodiments, the present disclosure pertains to a method for fabricating a three-dimensional artificial heart muscle (AHM) patch. In some embodiments, the method comprises obtaining and/or isolating cells from a subject. In some embodiments, the cells are primary cardiac cells. In some embodiments, the subject is a mammal. In some embodiments, the cells obtained and/or isolated are neonatal cardiomyocytes. In some embodiments, the neonatal cardiac myocytes are mammalian neonatal cardiac myocytes. In some embodiments, the method further comprises forming a scaffold. In some embodiments, the scaffold comprises fibrin gel scaffold. In some embodiments, the method comprises seeding the cells in the fibrin gel scaffold. In some embodiments, the method comprises culturing the cells seeded in the fibrin gel under conditions appropriate for the formation of an artificial heart muscle (AHM) patch. In some embodiments, the method comprises using anchors to control the geometry of the patch. In some embodiments, the method further comprises assessing the structure and function of the AHM patch formed by the method disclosed herein.

Confocal analysis of the AHM indicates structural similarity to native heart muscle, (FIG. 11B) and measured twitch forces represent a high degree of functionality. In some embodiments of the present disclosure, fibrin gel was used as a scaffold as the two main components, fibrinogen and thrombin, can be isolated from human blood so patient specific scaffolds can be created. In some embodiments, the method disclosed herein allows for the control of the geometry of the final patch formed to fabricate AHM shape to fit a particular application.

The AHMs generated by the methods disclosed herein may be of a variety of shapes. In certain embodiments, the shape of the AHMs, include, but are not limited to square, octagonal, rectangular, triangular, and circular. In some embodiments, the size of the AHMs ranges from about 2 $cm^2$ to about 3 $cm^2$. In some embodiments, the AHMs generated by the methods disclosed herein may be octagonal. Octagonal geometries afforded the most efficient means of coverage of the perimeter of decellularized hearts while requiring the fewest resources. High twitch forces along with a readily reproducible and bioactive scaffold render the AHM model of the present disclosure an efficient mechanism for delivery of cells to a structurally sophisticated scaffold.

Figure 6:
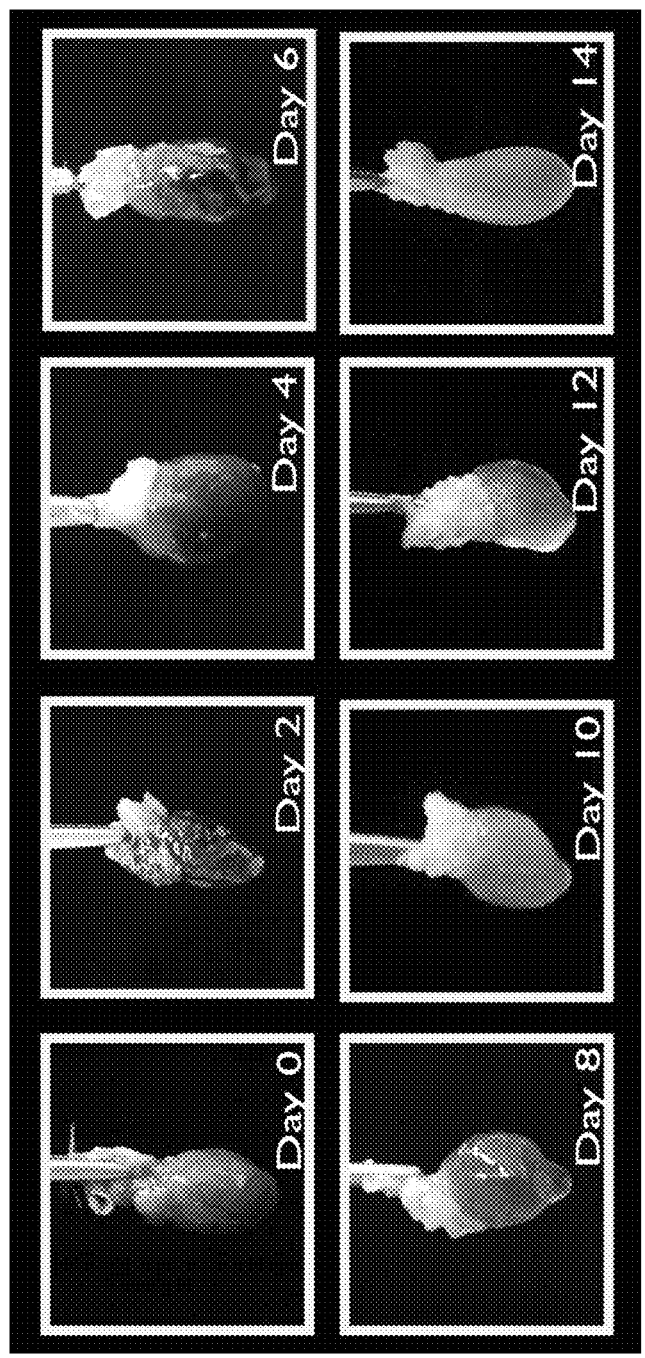
FIG. 6 shows stages of decellularization process over time. Progress of decellularization of the rat hearts at 2-day increments over 14 days.
Figures 7A, 7B:
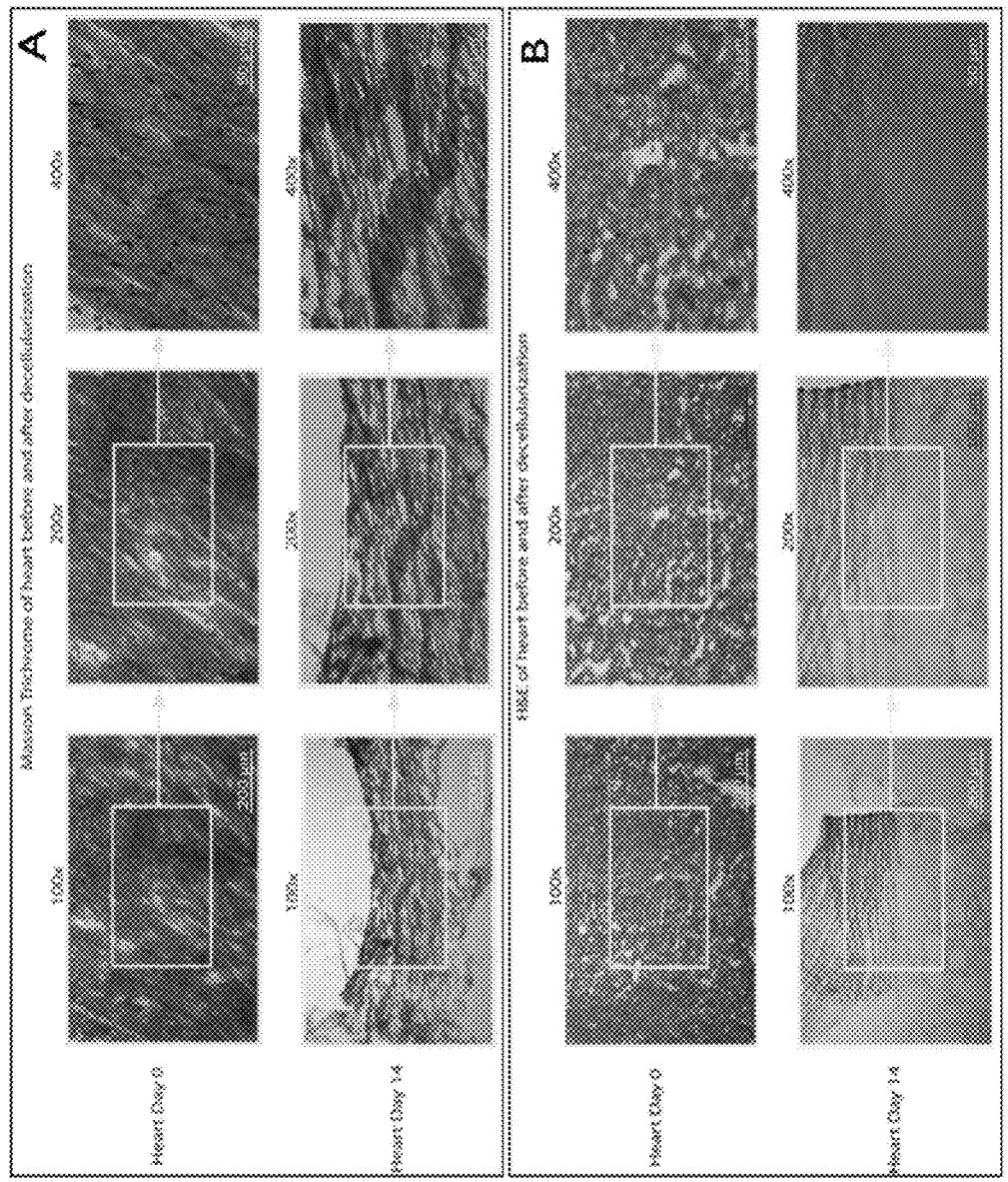
FIGS. 7A-7B show histology of the decellularized hearts. Masson's trichome stains of the heart tissue prior to (day 0) and after (day 14) the completion of the decellularization process viewed using 100×, 200×, and 400× objectives (FIG. 7A). H&E stains ECM heart tissue prior to day 0 and after day 14 the completion of the decellularization process with 100×, 200× and 400× objectives.

In some embodiments, the decellularization process occurs over the course of about 14 days. (FIG. 6). In some embodiments, the decellularization solutions were not actively perfused through the hearts. In some embodiments, the decellularization comprised of simple submersion and agitation of the hearts in a decellularization solution. After completion of the decellularization process, the remaining extracellular matrix structures appeared macroscopically intact. Vessels, ventricles and atriums are visible inside of the translucent structures. H&E and Masson's trichrome stains of the decellularized constructs show striated ECM networks with no cellular presence. (FIG. 7). Confocal images of the decellularized scaffold show a collagen rich network containing no cells. High-resolution images reveal empty spaces ~5-10 μm in diameter where cells were located prior to decellularization of the hearts indicates the efficiency of the decellularization protocol.

In some embodiments, the present disclosure pertains to a method for the formation of a bioartificial heart (BAH). In some embodiments, such a method comprises obtaining and/or isolating cells from a subject. In some embodiments, the cells are primary cardiac cells. In some embodiments, the subject is a mammal. In some embodiments, the cells obtained and/or isolated are neonatal cardiomyocytes. In some embodiments, the neonatal cardiac myocytes are mammalian neonatal cardiac myocytes. In some embodiments, the method further comprises obtaining a scaffold. In some embodiments, the scaffold is obtained by decellularization of a heart tissue. In some embodiments, the method further comprises transplanting the cells within the scaffold. In some embodiments, the transplanting the cells is by direct cell transplant. In some embodiments, the direct cell transplant comprises delivering the cells to the acellular scaffold by a plurality of direct injections. In some embodiments, the method further comprises culturing the scaffold transplanted with the cells in a perfusion culture apparatus. In some embodiments, the perfusion culture apparatus mimics in vivo conditions.

In some embodiments the present disclosure relates to a method for the formation of a bioartificial heart (BAH). In some embodiments, the method comprises fabricating a 3-dimensional AHM patch by the aforementioned method. In some embodiments, the method further comprises obtaining a scaffold. In some embodiments, the scaffold is obtained by decellularization of a heart tissue. In some embodiments, the method further comprises recellularization of the scaffold with the AHM patch. In an embodiment, the recellularization comprises using a plurality of the AHM patches. In some embodiments, the recellularization of the scaffold comprises inverting the fabricated AHM and placing the decellularized scaffold on the surface. In some embodiments, the method further comprises suturing the plurality of AHMs around the decellularized scaffold. In some embodiments, the recellularization comprises direct cell transplant into the scaffold. In some embodiments, the recellularization further comprises using at least one AHM patch in conjunction with the direct cell transplant. In some embodiments, the at least one AHM functions as a barrier to hold the transplanted cells within the scaffold. In some embodiments, the AHM functions to provide contractile support to the BAH. In some embodiments, the plurality of AHMs partially cover the scaffold. In some embodiments, the plurality of AHMs completely cover the scaffold.

Cells aggregate on the upper surface of the fibrin gel in an AHM. Inverting the AHM exposes the cells to the outer surface thereby insuring more effective nutrient delivery from culture media to the cells of the AHM. Initial studies performed without inversion of the AHM resulted in lower contraction of the construct perhaps due to limited nutrient delivery. After attachment of the AHM, BAHs were placed in static culture during which they experienced a period of latency of 1-2 days with no observable contraction. After culture for 4 days, slight pulling of the exterior AHM did not cause the fibrin layer to detach from the decellularized surface. This indicates some degree of interaction between the fibrin scaffold and the extracellular matrix (ECM) of the decellularized heart.

AHM represents an effective delivery vehicle for functional cardiomyocytes to the decellularized scaffold. Passive seeding of cells into a decellularized matrix, through coating or injection is an inefficient process, as most cells wash out of the matrix. The biologically active fibrin matrix contains functional sites at which cells can bind more readily. Physically combining the AHM with a structurally complex decellularized scaffold represents an alternative strategy for delivery of cells to a biologically similar matrix.

Noticeable contractility was observed around the entire perimeter of BAH constructs. While the contraction was typically microscopic, observable contraction indicates retention of basic myocardial function. Introduction of electrical pacing and perfusion may improve contraction rates and overall contractile force. Continually, only 4 million cells were used in order to produce the AHM tissue, while a typical adult rat heart is estimated to have approximately 100 million cells. Confocal staining of cross-sections of the samples indicated 3 main components: a cell-rich layer, a fibrin scaffold and a decellularized matrix. (FIGS. 11A-11B) Positive stains for α-actinin, a protein found in Z-discs of cardiac muscle, confirm the presence of cardiomyocytes in the BAH constructs. Positive collagen stains indicate healthy cells in the cell-rich layer. Furthermore, the collagen network visualized in confocal images of the decellularized scaffold is structurally complex and contains no cells. (FIG. 11A) The synchronicity of biopotential peaks in channels 1-8 indicates a degree of cell-cell interactivity. (FIG. 12)

Figure 8:
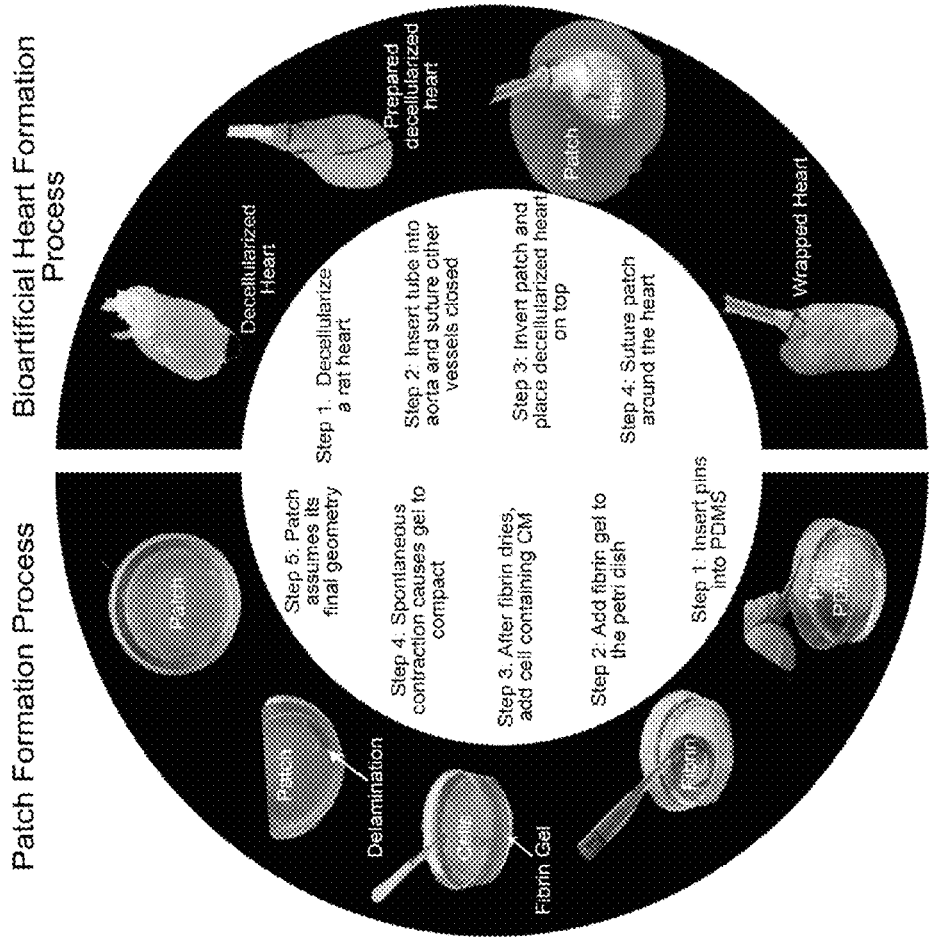
FIG. 8 shows stages of the bioartificial heart (BAH) formation process. Representative images of the various stages of the fabrication process for the bioartificial hearts. The left side of the figure illustrates the stages of the AHM fabrication process and the right side shows the various steps when constructing the total artificial heart. Adult Sprague Dawley rat hearts are subjected to a decellularization protocol to form a decellularized scaffold. The AHM is secured around the perimeter of the decellularized scaffold to promote contractile function.

While channels 1-8 represent the biopotentials at 8 distinct locations across the construct, the peaks and troughs of the biopotential readings are relatively well matched. Variations in the biopotential amplitudes amongst electrodes may be due to minor variations in cell density at different locations around the BAH. Constructs were not paced prior to measurement, indicating the AHMs ability to self-pace. Furthermore, the spontaneous contractile frequency measured in FIG. 8 is approximately 4.5 Hz, which is similar to the resting heart rate of a newborn rat.

The methods described for generation of BAH constructs characterize an original protocol for establishing the framework of a tissue-engineered heart. Advanced tissue engineered heart muscle with a bioactive scaffold and a high twitch force represents a novel vehicle for cellular delivery. A decellularized and highly structured scaffold allows potential for future sophistication and adaptability of the concept. Combination of the two allows for the inception of contractile and pumping ability to a structurally complex, natural heart scaffold. Static culture of tissue-engineered constructs is a limited technique and generally unsuitable for 3D tissue culture. True tissues in vivo are constantly subjected to a variety of stimuli, which direct the form and function of cells in the tissues. As such, it is essential to recreate some of the aspects of the in vivo environment in order to ensure enhanced performance and viability of tissue-engineered constructs. Towards this end, the present disclosure contemplates the use of bioreactors for enhancing BAH function, including an electrical stimulation and a dual-purpose perfusion bioreactor, with the ability to perfuse media and provide mechanical stimulation simultaneously.

While inclusion of AHM to the outer surface of the constructs is an efficient means of cellular delivery, there was little cellular penetration into the decellularized scaffold. Recellularization of the decellularized matrix must occur in order to produce a more innate structure. The current model is formed using only 4 million cells per heart. Consequently, in order to improve construct similarity to native tissue, the present disclosure contemplates adding more cells. One potential seeding method involves using ε-aminocaproic acid. The acid is added during culture of the AHM to reduce degradation of the fibrin gel. If the acid is not added after construct formation, degradation of the gel occurs resulting in the deposition of a thin layer of cells to the outer surface of the decellularized matrix. If this process is repeated to embed multiple layers of AHM, it could represent an effective means of delivering a high number of cells to the construct.

Another method of deposition of cells to the decellularized matrix involves direct injection. Unfortunately, direct injection is a relatively inefficient method with the majority of the cells washing out in culture. In order to overcome this limitation, the present disclosure contemplates pretreatment of cardiac myocytes with linker molecules or integrin stabilizers such as Manganese Chloride ($MnCl_2$) to increase the efficiency of attachment of directly injected cells. The present disclosure pertains to a method establishing the framework for the formation of a bioartificial heart construct. The present disclosure also pertains to sophisticated tissue engineered heart muscle along with a highly organized decellularized scaffold for the development of a true total bioartificial heart.

In some embodiments, the present disclosure pertains to a method of treatment of cardiac tissue injury in a subject in need thereof. In some embodiments, the method includes implanting the aforementioned AHM in the injured area of the subject.

In some embodiments, the present disclosure pertains to a method of treatment of a congenital heart disease, acute or chronic stress (e.g., systemic hypertension, pulmonary hypertension or valve dysfunction), atheromatous disorders of blood vessels (e.g., coronary artery disease), ischemia, infarction, inflammatory disease and cardiomyopathies or myocarditis, congestive heart failure. In some embodiments, the method comprises replacing the natural heart with the aforementioned bioartificial heart (BAH), in a subject in need thereof.

Additional embodiments of the present disclosure pertain to a medicament comprising the aforementioned composition. In some embodiments the medicament further comprises at least one agent from the group consisting of survival factors, growth factors, pharmacological agents, angiogenic factors, beta-blockers or ACE inhibitors.

Advantages and Applications

The methods of the present disclosure may be utilized to make three-dimensional artificial cardiac patches for various applications. For instance the methods of the present disclosure may be used for repairing cardiac tissue injuries and congenital heart defects. The methods of the present disclosure may also be used for the development of biocompatible, adaptive, non-immunogenic materials for cardiac tissue replacement. The three-dimensional artificial cardiac patches of the present disclosure revealed better contractility than ever reported before for engineered cardiac tissue. Additionally, the cardiac patches of the present disclosure display abundant vascularization and robust cellular division. Furthermore, in some embodiments of the present disclosure, the patches may be constructed using host origin fibrinogen and thrombin to produce the non-immunogenic fibrin scaffold before in vivo application.

Reference will now be made to various embodiments of the present disclosure and experimental results that provide support for such embodiments. However, Applicants note that the disclosure herein is for illustrative purposes only and is not intended to limit the scope of the claimed subject matter in any way.

Example 1

Methods

All animal protocols were approved by the Institutional Animal Care and Use Committee (IACUC) at the University of Houston, in accordance with the "Guide for the Care and Use of Laboratory Animals" (NIH publication 86-23, revised 1996). All materials were purchased from Sigma-Aldrich (St. Louis, Mo.) unless otherwise specified.

Example 2

Isolation of Primary Cardiac Cells

Cardiac cells were isolated from the hearts of 2-3 day old neonatal Sprague-Dawley rats using an established method. Briefly, each heart was cut into 3-4 pieces in an ice-cold phosphate buffer consisting of 116 mM NaCl, 20 mM HEPES, 1 mM $Na_2HPO_4$, 5.5 Mm glucose, 5.4 mM KCl and 0.8 mM $MgSO_4$. After blood cells were rinsed out, heart pieces were transferred to a dissociation solution consisting of 0.32 mg/ml collagenase type 2-filtered (Worthington Biochemical Corporation, Lakewood, N.J.) and 0.6 mg/ml pancreatin in phosphate buffer. The hearts were cut into 1-$mm^2$ pieces and then transferred to an orbital shaker and maintained at 37° C. for 30 minutes at 60 rpm. At the end of the digestion process, the supernatant was collected in 3 ml of horse serum to neutralize the enzyme and centrifuged at 1000 rpm for 5 minutes at 4° C. The cell pellet was resuspended in 5 ml horse serum and kept in an incubator at 37° C. supplied with 5% $CO_2$. Fresh dissociation solution was added to the partially digested tissue and the digestion process was repeated an additional 2-3 times. Cells from all the digests were pooled, centrifuged and suspended in culture medium consisting of M199 (Life Technologies, Grand Island, N.Y.), with 20% F12k (Life Technologies, Grand Island, N.Y.), 10% fetal bovine serum, 5% horse serum, 1% antibiotic-antimycotic, 40 ng/ml hydrocortisone and 100 ng/ml insulin. Cell viability was analyzed by Trypan blue (4%) staining according to the manufacturer's protocol.

Example 3

Preparation of Acellular Scaffolds and Fabrication of BAHs

FIG. 1 shows the schematic method for fabrication of BAHs. Rat hearts were obtained from 3-4 month old female Sprague-Dawley rats and immediately washed in a phosphate buffered saline solution to prevent blood coagulation. The hearts were then sequentially incubated in 15 mL of a series of decellularization solutions. Five solutions were made with the following compositions: Solution 1 (S1), 80% glycerol+0.9% NaCl+0.05% $NaN_3$+25 Mm EDTA; S2, 4.2% sodium deoxycholate+0.05% $NaN_3$; S3, 1% SDS+0.05% $NaN_3$; S4, 3% Triton X-100+0.05% $NaN_3$ and S5, 0.05% $NaN_3$. Over a 16 day period, the hearts were exposed to the solutions in the following order: days 1, 2 in 51; days 3-5 in S2; days 6-7 in S1; days 8-9 in S3; days 10-11 in S4; days 12-13 in S3; and days 14-16 and after in S5 (Table 1). Before use, the hearts were perfused and rinsed with sterile DPBS for 15 minutes.

TABLE 1

| Solution/Properties | Components | Schedule |
|---|---|---|
| Solution 1: Fixing agent/Detergent | 80% Glycerol (by volume) 0.9% NaCl 0.05% $NaN_3$ 25 mM EDTA | Day 0-2 |
| Solution 2: Detergent | 4.2% sodium deoxycholate 0.05% $NaN_3$ | Day 2-4 |
| Solution 3: Detergent | 1% SDS 0.05% $NaN_3$ | Day 4-6 Day 8-10 |
| Solution 4: Detergent | .05% $NaN_3$ | Day 12-14 |
| Solution 5: Detergent | 3% Triton X-100 (by volume) 0.05% $NaN_3$ | Day 6-8 Day 10-12 |

The newly-recellularized heart was cannulated to the aorta using a 16 gauge needle, suspended within a culture vessel and placed in a Langendorff perfusion system, and perfused with culture media mentioned above. Culture media reservoir was maintained at an elevated position (100 cm) to drive the gravity fed perfusion. The system was housed in an incubator for temperature and pH regulation (FIGS. 2I, 2J). The 2-ml cell suspension containing 50 million cells was injected into multiple regions in the acellular heart. After a 24 hour culture period, a second set of 50 million cells were injected into the same heart. Spent media was collected and recirculated to the heart using a peristaltic pump, which was placed outside the incubator; fresh media was replaced every 2 days.

Example 4

ECG and Ventricular Pressure Measurements

Electrocardiogram (ECG) signal was measured using Octal Bio Amp (ML138, ADinstrument, Colorado Springs, Colo.). Data was acquired through a 16 channel PowerLab-system (PL3516/P, ADInstruments). ECG of the heart was detected by inserting the needle anode (MLA1213, ADInstruments) into the lateral wall of left ventricle 15, attaching the cathode onto the right atrial appendage and the ground onto the aorta (FIG. 2K). LabChart (ADInstruments) was used for data analysis. The ECG analysis module was used to calculate the QRS wave amplitude. BAH ventricular pressure was measured using a 3.5 F high fidelity, catheter-tipped micromanometer (model SPR-524, Millar Inc.). The left atrium was cut and the catheter was inserted through the mitral valve and advanced into the LV chamber. Then the catheter was similarly placed into the right ventricle (RV) through the right atrium and tricuspid valve for RV measurements. Measurements were recorded for 30-60 seconds. The output from the Millar catheter was recorded using PowerLab system.

ECG signal and ventricular pressure from normal control hearts were assessed as previously described. The hearts from 3-4 month old female Sprague-Dawley rats were excised and immersed immediately in ice-cold K—H solution (4° C.), which consists of NaCl 119.0 mmol/L, KCl 4.7 mmol/L, $NaHCO_3$ 25.0 mmol/L, $KH_2PO_4$ 1.2 mmol/L, $MgSO_4$ 1.2 mmol/L, $CaCl_2$ 2.5 mmol/L and Glucose 11.0 mmol/L. Within 30 seconds, the aorta was mounted onto a cannula, and retrogradely perfused under a Langendorff system (Radnoti, LLC. Monrovia, Calif.) with K—H solution (37° C., pH 7.40) at 100 cm $H_2O$ aerated with 95% $O_2$+5% $CO_2$.

Example 5

Histology and Immunofluorescence

For assessment of cellular distribution within BAHs, whole heart sections of 10 µm thickness were stained with Masson's Trichrome reagents according to the manufacturer's protocol. Section images were taken under a light microscope and the images of whole heart sections were stitched together using the Grab Large Image model within software NIS Elements 4.13 (Nikon Instruments Inc., Melville, N.Y.). The distinct cellular components were differentiated to validate observed functionality. Whole heart sections of 10 µm thickness were fixed in ice-cold acetone for 10 minutes; nonspecific epitope antigens were blocked with 10% goat serum at room temperature for 1 hour. Sections were incubated with specific mouse anti-α-actinin antibody (Sigma, Catalog No A7811) 1:200, rabbit anti-collagen type I (Abcam, ab34710) 1:100, rabbit anti-connexin 43 (Cx43) (Abcam, ab11370) 1:100, rabbit anti-N-cadherin (Abcam, ab12221) 1:150, and rabbit anti-von Willebrand factor (vWF) (Abcam, ab6994) 1:750 at room temperature for 1 hour. Subsequently, sections were treated with goat anti-mouse or goat anti-rabbit secondary antibodies (Alexa Fluor 488 and Alexa Fluor 546, Life Technologies, Grand Island, N.Y.) 1:400 at room temperature for 1 hour. Nuclei were counterstained with 4,6-diamidino-2-phenylindole (DAPI) (2.5 µg/ml) for 5 min at room temperature. Fluorescence images were obtained with a Nikon C2+ confocal laser scanning microscope (Nikon Instruments Inc., Melville, N.Y.).

Example 6

Decellularization of Rodent Hearts

We used a detergent based decellularization process that has been developed and used extensively for several cardiovascular and musculoskeletal tissue engineering applications. Over a course of 16 days (FIG. 2), the freshly harvested rat heart is subjected to different detergent solutions. The effectiveness of decellularization can be judged by several metrics, the first of which is visual inspection. Based on visual inspection, we observed a gradual decrease in the opacity of the rat hearts. Freshly isolated rat hearts were visibly pinkish red (FIG. 2A), and during the course of the decellularization process the color of the hearts changed to a light brown and whitish color (FIGS. 2B-2H). In order to validate the removal of cellular components, sections from decellularized hearts were stained with Masson's trichrome reagents and also examined with immunofluorescence staining of α-actinin and nuclei. In FIGS. 3A1 and 3A2 showed cardiac muscle cells and nuclei from a normal heart, FIGS. 3B1 and 3B2 demonstrated that decellularized tissue section did not keep any cardiomyocytes and nuclei. Thus, based on these results, we were able to obtain decellularized heart scaffolds that could serve to fabricate BAHs.

Example 7

Fabrication of BAHs

We used cell transplantation to support the fabrication of BAHs. Fifty million cells were used to populate the interior of acellular hearts at the time of initial cell seeding. Twenty-four hours after initial cellularization, a second batch of 50 million cells was used to populate the same graft. This process resulted in spontaneously contractile BAHs within 2 days of the second cellularization. The rate of contraction was visibly determined to be 50-80 bpm. Maximum amplitudes of contraction were observed at day 4 or 5, after which they decreased gradually. At 8 days after cell injection, contraction was nearly invisible. Based on visual indicators, our strategy for the fabrication of BAHs was validated. We assessed the histological properties of BAHs using Masson trichrome and immunofluorescence stainings (FIG. 3). Both of these methods confirmed the presence of a large number of cells that were distributed throughout the acellular graft. We obtained images from different regions of the recellularized hearts and observed cellular presence throughout the constructs. A higher concentration of cells were observed in the LV inferior (FIGS. 3D1 and D2) and LV lateral walls (FIGS. 3E1 and E2) than in the RV anterior wall (FIGS. 3C1 and C2). From RV to LV, sequential sections were made and stained with Masson's trichrome reagents. FIGS. 3F1-3F6 illustrate more pronounced heart muscle growth in the LV than in the RV. The immunofluorescence image from the LV inferior wall was positive for collagen type I (FIG. 3H) indicating potential ECM production and support. Positive stainings for connexin 43 (FIG. 3I) and N-cahderin (FIG. 3J) indicate that the recellularized cardiac tissue maintained electromechanical coupling, which sustains electrical propagation between cardiac cells. In these sections, there also were abundant vWF signals, which are markers of endothelial cells.

Example 8

Functional Properties of BAHs

We measured the functional performance of BAHs based on ECG properties (FIG. 4A) and ventricular pressure (both left and right ventricles) of BAHs (FIG. 4B). For both the ECG and pressure measurements, freshly isolated rat hearts were used as positive controls. In the case of the ECG measurements, we determined the maximum amplitude to be 0.8 mV with a contraction rate of 65 bpm, compared with 2.75 mV and 250 bpm for freshly isolated rat hearts. We also measured the pressure within the left and right ventricles of BAHs. In both cases, we determined an average heart rate of 65 bpm, compared with 250 bpm for positive controls. The average heart-rate of LV and RV was found to be very similar without any notable differences between the two. We did, however, notice a significant difference in the amplitude of the peaks obtained for the left and right ventricle of the BAHs. As can be seen in FIG. 4B, the maximum pressure obtained for LV was found to be 0.35 mmHg, while the maximum pressure obtained for RV was 0.15 mmHg; however, the maximum pressure from the control LV is 120 mmHg and that from control RV is 25 mmHg. The contraction of a representative recellularized heart on day 5 after cell injection was determined to be 68 bpm.

Example 9

Fabrication of Artificial Heart Muscle (AHM)

Figure 5:
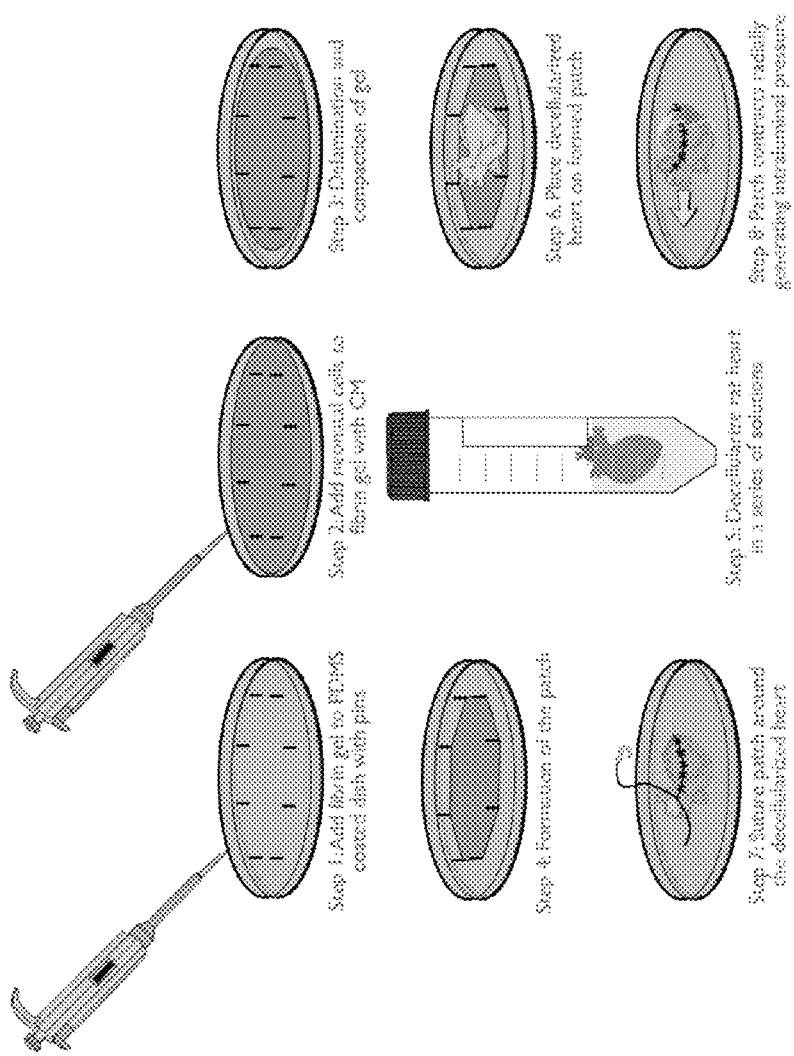
FIG. 5 shows a schematic of a method for bioartificial heart formation. AHM is created using neonatal cardiac cells and fibrin gel. Adult hearts are subjected to a decellularization protocol to form a decellularized scaffold. The AHM is secured around the perimeter of the decellularized scaffold to promote contractile function.

The heart muscle was fabricated using fibrin gel and neonatal cardiomyocytes (FIG. 5 and FIG. 8). A 35 mm tissue culture plate was coated with 2 ml of SYLGARD (PDMS, type 184 silicone elastomer) (Dow Chemical Corporation, Midland, Mich.). The plate was air dried for 2 weeks and sterilized with 80% ethanol before use. Eight minutien pins (Fine Science Tools, Foster City, Calif.), 0.1 mm diameter, were placed in the culture plate to form a regular octagon with a radius of 1.3 cm, a square with 2 cm and a square with 3 cm edges. 45 Mixing 1 mL of culture media containing 10 U thrombin/mL with 500 μL of saline containing 20 mg/mL fibrinogen in a PDMS coated petri dish allowed for the formation of a fibrin gel scaffold. The petri dishes were shaken well to promote mixing and placed in the incubator in order to promote gel formation within 15 minutes. Cells were seeded with a density of 4M per plate. Epsilon-aminocaproic acid (2 mg/mL) was added to the culture plate to inhibit the fibrinolysis by endogenous proteases. The cells were cultured in an incubator at 37° C. and 5% CO2 with CM changes every two days.

Example 10

Contractile Twitch Force of AHM

From day 4, twitch force was measured using a high sensitivity isometric force transducer (MLT0202, ADinstruments, Colorado Springs, Colo.), connected to a quad bridge amplifier (FE224, ADinstrument, Colorado Springs, Colo.). Data acquisition was performed through a 16 channel PowerLab system (PL3516/P, ADInstruments, Colorado Springs, Colo.). The force transducer arm was attached to one free-corner of the patch, while the other ends were held fixed; spontaneous measurements were recorded for 30-60 seconds. Pretension was adjusted using a micro-manipulator (Radnoti LLC, Monrovia, Calif.) and measurements of spontaneous contraction were recorded. A Stable-Temp hotplate (Cole-Parmer, Vernon Hills, Ill.) was used to maintain media temperatures at 37° C. throughout the course of measurement. LabChart's (ADInstruments, Colorado Springs, Colo.) peak analysis module was used to calculate the maximum twitch force and baseline force (pretension).

Example 11

BAH Formation

Decellularized heart scaffolds were washed 3 times and placed in PBS 24 hours prior to construct formation to wash out decellularization solutions. At 4-6 days after plating, most AHM tissues were fully formed. The anchoring minutien pins were gently removed from the AHM. The artificial muscle was then lifted using two forceps and delicately inverted on the petri dish surface. Artificial heart tissues were re-pinned to the PDMS using minutien pins. The decellularized heart scaffolds were placed on the inverted tissues. The AHM was unpinned and gently sutured around the outside of the decellularized scaffolds using sterile 6-0 polypropylene sutures (AD Surgical, Sunnyvale, Calif.). The completely wrapped construct was suspended in a 50 mL conical tube by a 1/16" diameter tubule inserted through the aorta of the decellularized construct. Subsequently, 15 mL of CM was added along with ε-aminocaproic acid (2 mg/ml), and the construct was placed in an incubator at 37° C. and 5% $CO_2$ with CM changes every two days and observed periodically for contraction.

Example 12

Contraction

Bioartificial hearts were examined daily for contractile action using an inverted phase-contrast microscope (Olympus, Center Valley, Pa.). Hearts were removed from culture and placed in a small amount of CM in a 60 mm petri dish coated with PDMS. Still photographs and videos were captured using a camera (Lumenera, Ottawa, ON) mounted on a light microscope. (Olympus, Center Valley, Pa.).

Example 13

Biopotential Measurement

Biopotential measurements were observed through the direct application of 8 electrodes to the construct after a period of culture. Constructs were placed in a PDMS coated petri dish with warmed media. A Stable-Temp hotplate (Cole-Parmer, Vernon Hills, Ill.) was used to maintain media temperatures at 37° C. throughout the course of measurement. Eight electrodes were pierced into the construct in a 4×2 grid with 2.54 mm of space horizontally between each electrode column and 3.8 mm of space vertically between each row. A reference wire was secured in PDMS in direct contact with the media at the edge of the dish. Electrodes were connected to an Octal Bio Amp (ML138, ADInstruments, Colorado Springs, Colo.). Data acquisition was performed through a 16 channel PowerLab system (PL3516/P, ADInstruments, Colorado Springs, Colo.). LabChart (ADInstruments, Colorado Springs, Colo.) was used to output the 8 measured channels into a table with a sampling rate of 1000 Hz over 2 minute periods. Matlab (Mathworks, Natick, Mass.) was used to analyze and process the data. A moving average smoothing function with an 8% span was applied to the data for all 8 channels to reduce noise.

Example 14

Histology

Histology was performed on natural and fully decellularized rat hearts and BAHs after 6 days of culture. Samples were all washed in PBS and gently patted dry using VWR® light-duty tissue wipers. Samples were suspended upright in a peel-a-way disposable embedding mold (VWR International, Radnor, Pa.) and submerged in liquid nitrogen for several seconds. Samples were then covered with Tissue Tek OCT (VWR International Radnor, Pa.) and placed immediately into a −85° C. freezer. Once samples were completely solid, each sample was cross-sectioned using a cryotome (Thermo Fisher Scientific, Waltham, Mass.). Tissue samples were cut at a thickness of 10-40 μm and placed on VWR® microslides. Cross-sections were stained with Masson's trichrome and H&E reagents according to manufacturer's protocol, and images were taken under the light microscope.

Example 15

Immunohistochemistry

Samples were frozen in OCT compound and sectioned to 10-40 μm thicknesses and placed on VWR® microslides. Cross-sections were fixed in ice cold acetone for 10 minutes; nonspecific epitope antigens were blocked with 10% goat serum at room temperature for 1 hour. Sections were incubated with mouse anti-α-actinin monoclonal antibody (Sigma, Catalog No A7811) 1:200 and rabbit anti-collagen type I (Abcam, ab34710) 1:100 at room temperature for 1 hour. Subsequently, sections were treated with goat anti-mouse and goat anti-rabbit secondary antibodies (Alexa Fluor 488 and Alexa Fluor 546, Life Technologies, Grand Island, N.Y.) 1:400 at room temperature for 1 hour. Nuclei were counterstained with 4,6-diamidino-2-phenylindole (DAPI) (2.5 μg/ml) for 5 min at room temperature. Fluorescent images were obtained with a Nikon C2+ confocal laser scanning microscope (Nikon Instruments Inc., Melville, N.Y.). Z-stack images were taken in order to examine 3D structures of sample slices with more than 20 μm thicknesses.

Example 16

Patch Formation

Established cell isolation methods were used to harvest cells with a viability of 81.0±2.2% (n=16). Delamination typically began at day 3 with patch formation usually completing by day 4 or 5. Contractile forces of patches plated with 4M cells using this method measured up to ~3,000 μN. Patches exhibited macroscopic spontaneous contractions after 2 days of culture. The frequency of spontaneous contraction was in the range of 1-5 Hz. Patches were observed to contract continuously and actively for upwards of 3 weeks.

Example 17

Decellularization

Hearts isolated from adult Sprague Dawley rats were subjected to a series of decellularization solutions as outlined in Table 1. The hearts became noticeably clearer and more translucent at each stage in the process. (FIG. 6) Hearts at day 0 and 14 of the decellarization process were sectioned and stained with H&E and Masson's trichrome staining. (FIG. 7) Sections of hearts at day 0 in the decellularization process exhibited typical H&E and Masson's trichrome patterns for untreated rat hearts. Masson's trichrome stains at day 14 contained only blue stains and revealed no nuclei. H&E stains at day 14 in the process showed only red stained networks with no nuclei.

Example 18

BAH Formation

Decellularized hearts were washed in PBS in order to remove sodium azide from the structures. Sodium azide typically lyses cells and if not washed, destroys viable cells from AHMs removing functionality of the construct. Patches were treated gently in order to avoid destroying fragile cardiac myocytes. Constructs were formed using both inverted and non-inverted heart muscle formation techniques. Cells tend to aggregate on the upper layers of the fibrin gel using normal AHM formation techniques. Inverting the heart muscle prior to wrapping exposed the majority of the functional cells to the outer surface. When heart muscle tissue was inverted, there was a noticeable increase in frequency of contraction of the artificial heart constructs viewed under the light microscope when compared with non-inverted muscle tissues.

Example 19

Contraction of BAH

After wrapping the patches around the outside of the decellularized hearts and securing them with sutures, contraction frequency would diminish or temporarily halt. After culturing the constructs for 1-2 days, contraction would resume at or near pre-wrapping frequency. Noticeable contractility was observed around the entire area of the heart under an inverted microscope. Observed contractile frequencies of beating BAHs ranged from 0.3 to 5 Hz.

Example 20

Morphology

Figure 9:
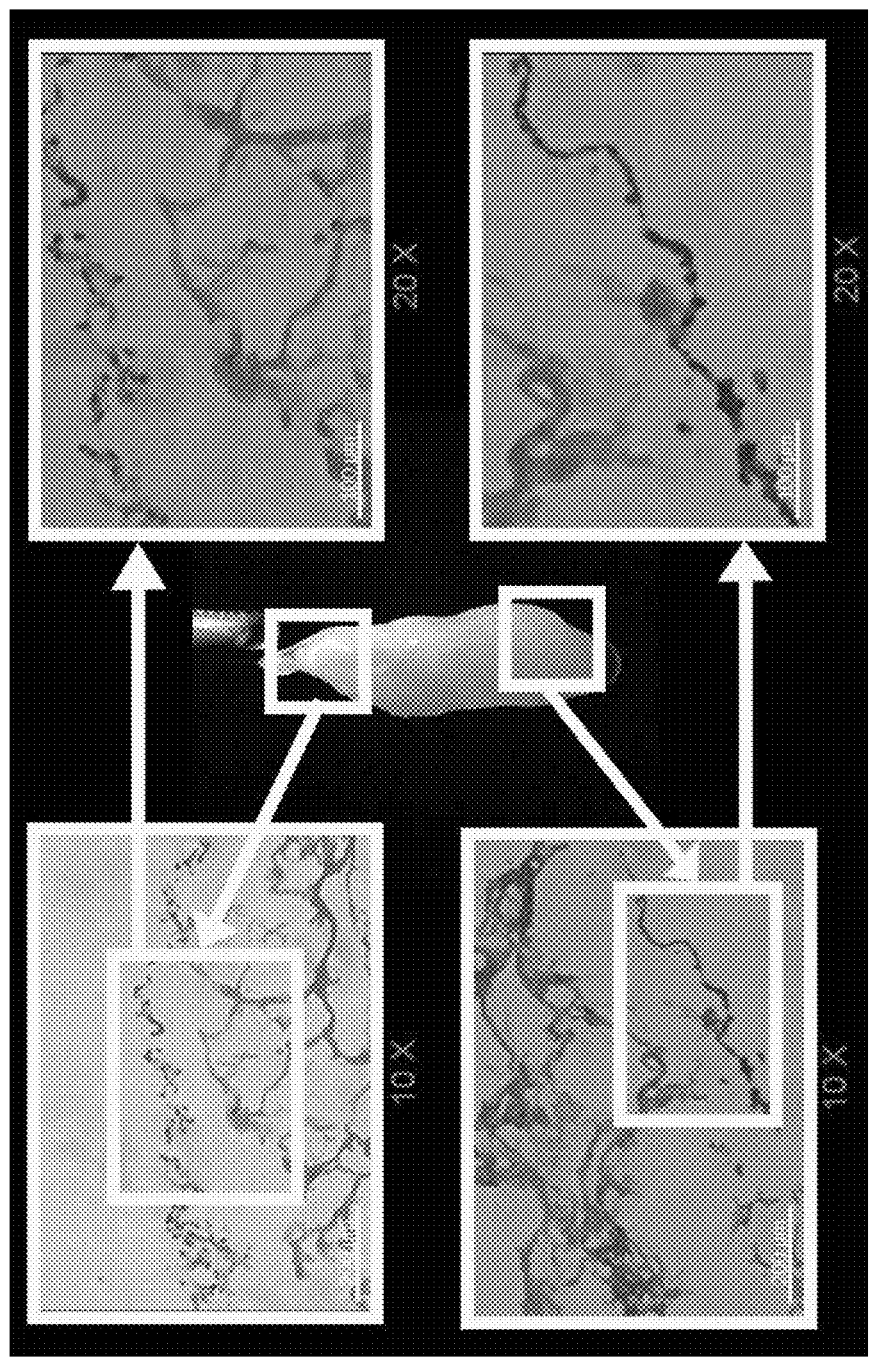
FIG. 9 depicts H&E staining of a cross-section of the total bioartificial heart (BAH). Cell nuclei are stained black and eosinophilic structures such as fibrin and collagen are stained pink.
Figure 10:
FIG. 10 shows a stitched image consisting of 28 (4×) images of a Masson Trichome stained cross-section of a BAH. It also contains a 20× portion of the cross-section. Collagen is stained blue, muscle fibers and fibrin are stained red and cell nuclei are stained black.

Cross-sections stained with H&E were positive for nuclear stain around the acellular scaffold, indicating the presence of cardiac cells. (FIG. 9) The cell-rich AHM layer is visible around the perimeter of each image. The interior portion contains completely decellularized ECM. Masson's trichrome stained cross-section of a BAH were imaged and stitched to visualize an entire cross-section. (FIG. 10). The exterior layer contains red stained fibrin gel and black stained cell nuclei. The interior portion is completely decellularized ECM with no noticeable black spots.

Example 21

Immunohistochemistry

Figures 11A, 11B:
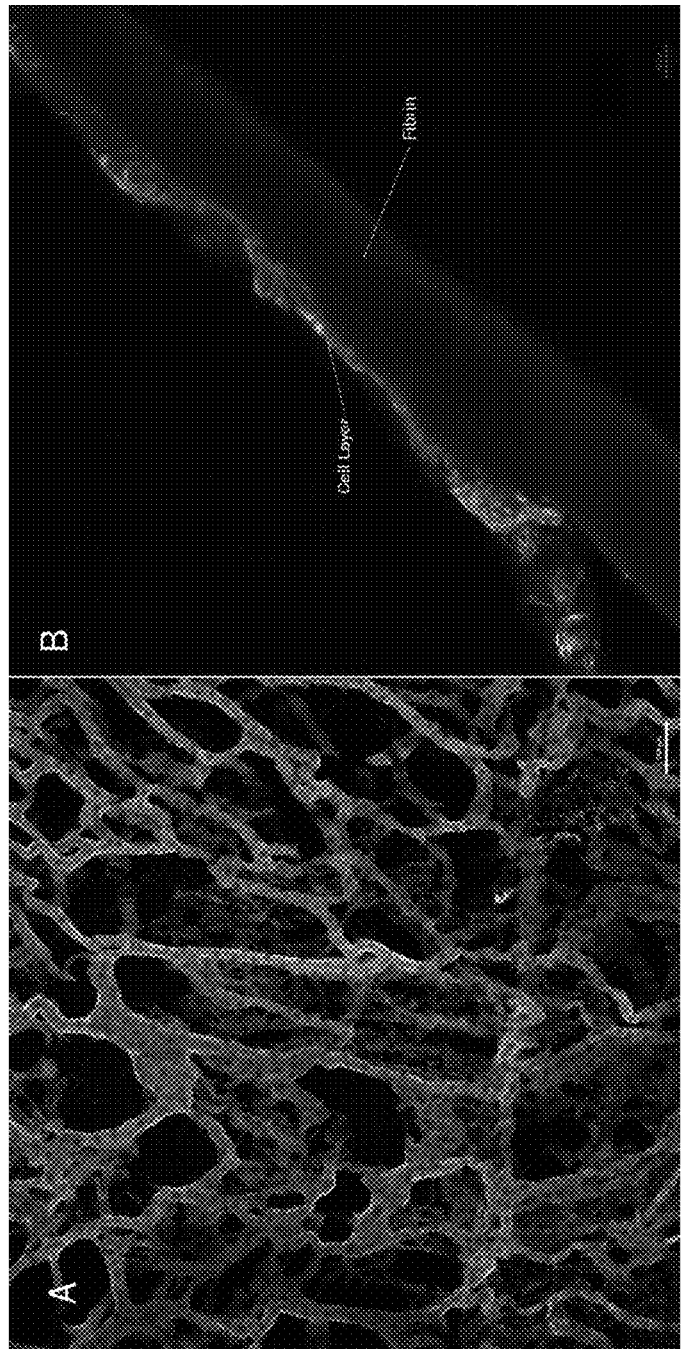
FIGS. 11A-11B show a confocal image of the cross-section of bioartificial heart (BAH). Immunofluorescence images of a cross-section of BAH stained for collagen (yellow) a-actinin (green), and DAPI (blue)

Confocal images contained fluorescently labeled structures highlighting collagen type I, α-actinin and cell nuclei. (FIGS. 11A-11B). Confocal images of the decellularized scaffold showed a collagen rich network with many apparent empty spaces dispersed throughout the network. (FIG. 11A) A cell rich layer containing collagen (yellow) α-actinin (green) and DAPI (blue) was found around the perimeters of the stained sections. (FIG. 11B).

Figures 13A, 13B, 13C:
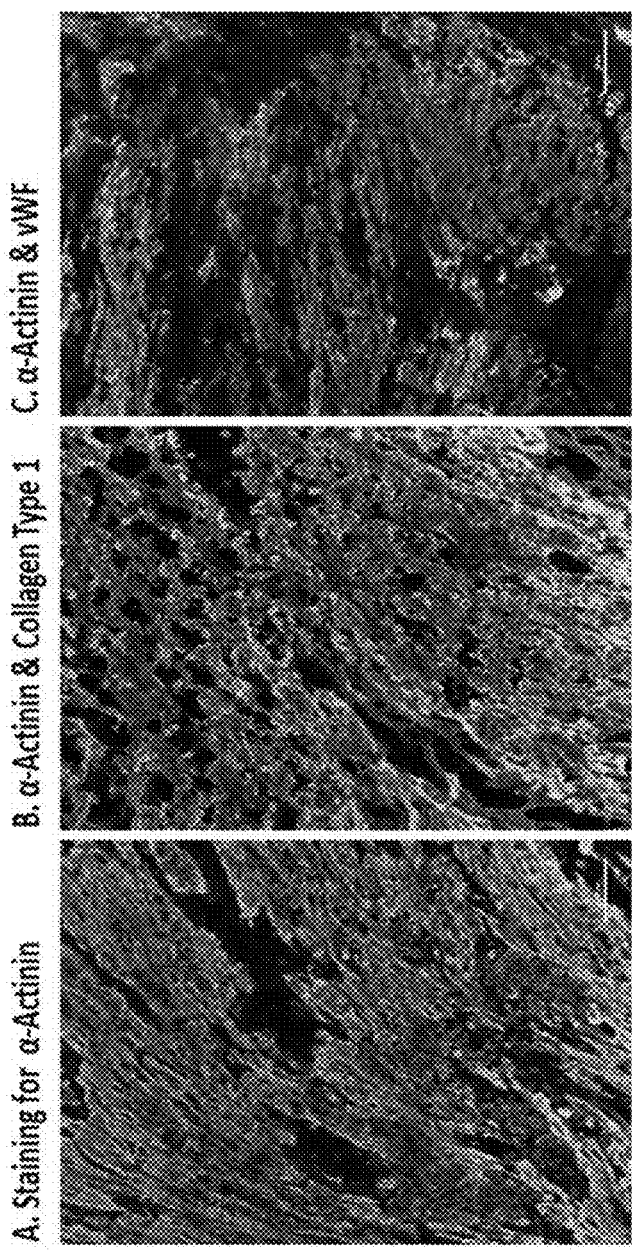
FIGS. 13A-13C show confocal imaging of BAHs fixed, sectioned and stained for antibodies against α-actinin (FIG. 13A), α-actinin and collagen type I (FIG. 13B) and α-actinin and vWF (FIG. 13C).

In order to visualize cardiac myocytes within BAHs, α-actinin staining was performed and confocal images obtained (FIG. 13A). As shown in FIG. 13A, there was an abundance of primary cardiac myocytes within the BAHs, based on positive staining for α-actinin. Furthermore, based on staining for collagen type I, the distribution of cells relative to the acellular graft was visualized (FIG. 13B). vWF staining was also performed to visualize uniformly distributed endothelial cells (FIG. 13C).

Example 21

Biopotential Measurements

Figure 12A:
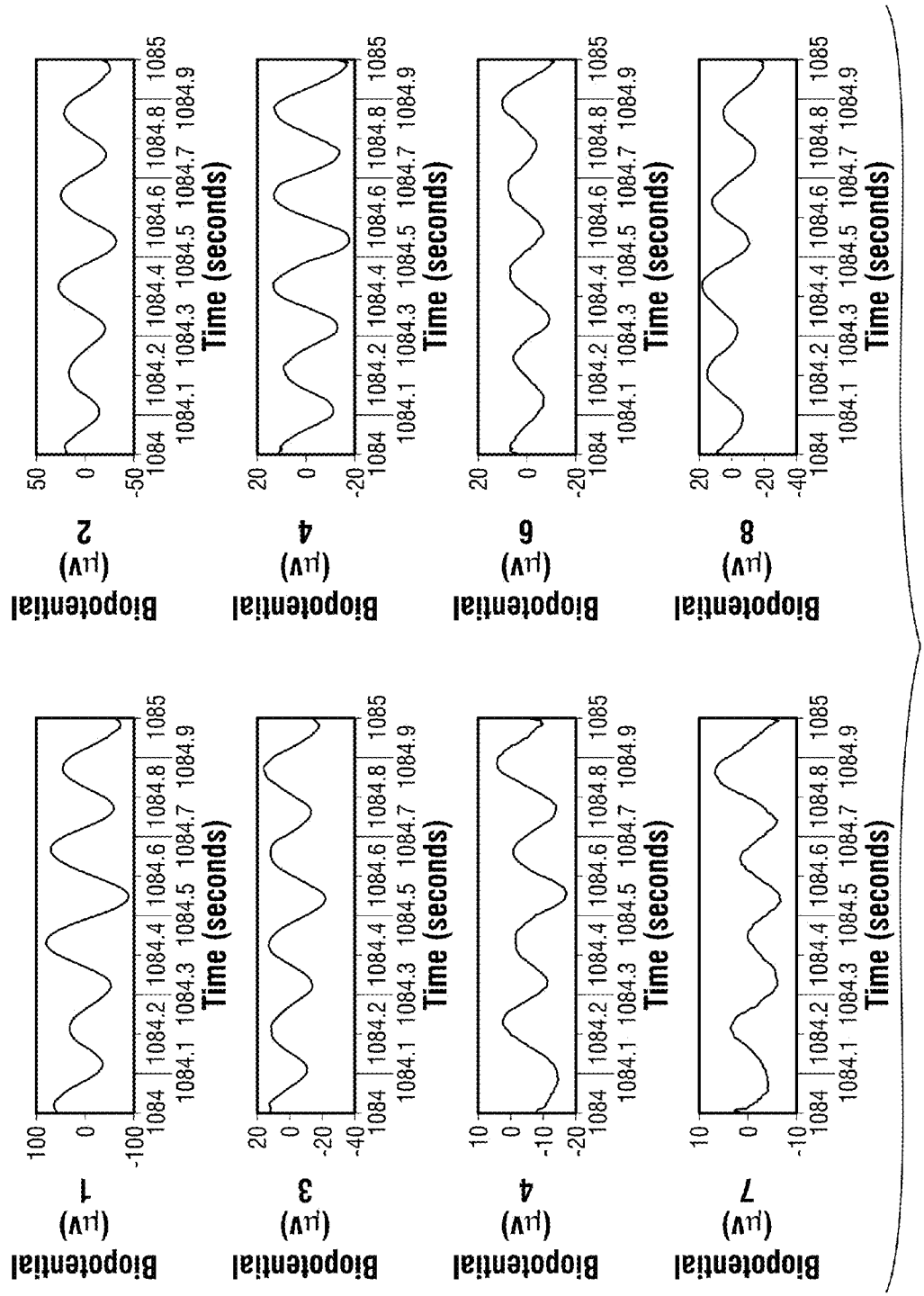
FIGS. 12A-12B show biopotential measurements of a beating BAH. Biopotential measurements over time for 8 electrodes are displayed in channels 1-8 (FIG. 12A). A schematic of the approximate placement of each electrode throughout the BAH sample is shown in FIG. 12B.
Figure 12B:
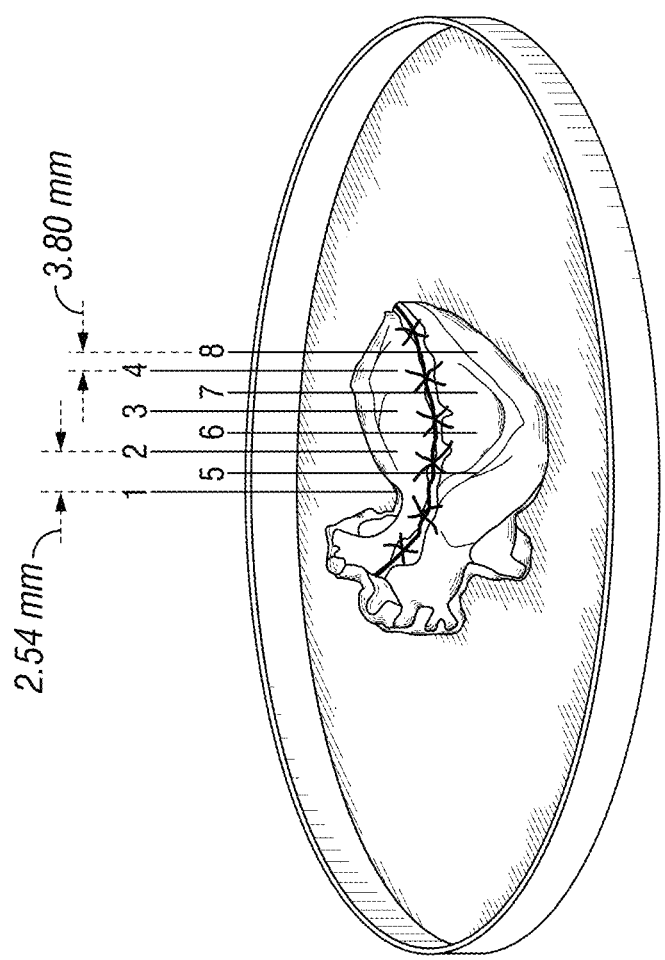

Synchronous contractility was observed across 8 electrode channels in a waveform pattern consistent with native heart muscle. (FIGS. 12A-12B). The sample measurement indicated a contractile rate of approximately 4.5 Hz with biopotential amplitudes in the range of 10-200 µV.

The embodiments described herein are to be construed as illustrative and not as constraining the remainder of the disclosure in any way. While the embodiments have been shown and described, many variations and modifications thereof can be made by one skilled in the art without departing from the spirit and teachings of the invention. Accordingly, the scope of protection is not limited by the description set out above, but is only limited by the claims, including all equivalents of the subject matter of the claims. The disclosures of all patents, patent applications and publications cited herein are hereby incorporated herein by reference, to the extent that they provide procedural or other details consistent with and supplementary to those set forth herein.

What is claimed is:

1. A method of fabricating a bioartificial heart comprising:
    obtaining and/or isolating cells from a subject;
    preparing a scaffold;
    transplanting the cells within the scaffold by direct cell transplant,
        wherein the direct cell transplant comprises delivering the cells to the scaffold by a plurality of direct injections; and
    culturing the scaffold transplanted with the cells in a perfusion culture apparatus, wherein the perfusion culture apparatus mimics in vivo conditions.

2. The method of claim 1, wherein the cells are primary cardiac cells.

3. The method of claim 1, wherein the subject is a mammal.

4. The method of claim 1, wherein the cells obtained and/or isolated are neonatal cardiomyocytes.

5. The method of claim 1, wherein the fabricated bioartificial heart has a spontaneous contraction frequency in the range of about 0.3 Hz to about 5 Hz.

* * * * *